(12) United States Patent
Singh et al.

(10) Patent No.: US 9,687,641 B2
(45) Date of Patent: Jun. 27, 2017

(54) METHOD AND DEVICE FOR TRANSDERMAL DELIVERY OF PARATHYROID HORMONE USING A MICROPROJECTION ARRAY

(75) Inventors: Parminder Singh, Union City, CA (US); Danir Bairamov, Irvine, CA (US); Guohua Chen, Sunnyvale, CA (US); Robert Wade Worsham, Cupertino, CA (US)

(73) Assignee: Corium International, Inc., Menlo Park, CA (US)

( * ) Notice: Subject to any disclaimer, the term of this patent is extended or adjusted under 35 U.S.C. 154(b) by 1328 days.

(21) Appl. No.: 13/101,071

(22) Filed: May 4, 2011

(65) Prior Publication Data
US 2011/0276028 A1    Nov. 10, 2011

Related U.S. Application Data

(60) Provisional application No. 61/331,226, filed on May 4, 2010.

(51) Int. Cl.
*A61M 37/00* (2006.01)
*A61K 9/00* (2006.01)

(52) U.S. Cl.
CPC ....... *A61M 37/0015* (2013.01); *A61K 9/0021* (2013.01)

(58) Field of Classification Search
CPC ............ A61K 9/0021; A61M 37/0015; A61M 37/0046; A61M 37/0053
USPC .......................... 604/46, 506, 289, 290, 307
See application file for complete search history.

(56) References Cited

U.S. PATENT DOCUMENTS

| | | |
|---|---|---|
| 1,554,510 A | 9/1925 | Kirby |
| 1,770,632 A | 7/1930 | Smith |
| 2,046,240 A | 6/1936 | Bayley |
| 2,434,407 A | 1/1948 | George |
| 3,675,766 A | 7/1972 | Rosenthal |
| 3,704,194 A | 11/1972 | Harrier |
| 3,814,097 A | 6/1974 | Ganderton et al. |
| 3,873,255 A | 3/1975 | Kalwaites |
| 3,918,449 A | 11/1975 | Pistor |
| 3,964,482 A | 6/1976 | Gerstel et al. |
| 4,055,029 A | 10/1977 | Kalbow |

(Continued)

FOREIGN PATENT DOCUMENTS

| | | |
|---|---|---|
| CA | 2376285 | 12/2000 |
| CA | 2316534 | 3/2001 |

(Continued)

OTHER PUBLICATIONS

Chun, et al., "An array of hollow microcapillaries for the controlled injection of genetic materials into animal/plant cells." IEEE Workshop on Micro Electro Mechanical Systems, pp. 406-411, (1999).

(Continued)

*Primary Examiner* — Kevin C Sirmons
*Assistant Examiner* — Deanna K Hall
(74) *Attorney, Agent, or Firm* — Jacqueline F. Mahoney; Judy Mohr; McDermott Will & Emery LLP

(57) ABSTRACT

A method and a drug delivery system for transdermally administering parathyroid hormone (PTH) in a pulsatile fashion are provided, where the drug delivery system comprises an array of microprojections each comprising PTH.

14 Claims, 7 Drawing Sheets

(56) References Cited

U.S. PATENT DOCUMENTS

| | | |
|---|---|---|
| 4,117,841 A | 10/1978 | Perrotta et al. |
| 4,151,240 A | 4/1979 | Lucas et al. |
| 4,180,232 A | 12/1979 | Hardigg |
| 4,342,314 A | 8/1982 | Radel et al. |
| 4,381,963 A | 5/1983 | Goldstein et al. |
| 4,395,215 A | 7/1983 | Bishop |
| 4,402,696 A | 9/1983 | Gulko |
| 4,460,368 A | 7/1984 | Allison et al. |
| 4,460,370 A | 7/1984 | Allison et al. |
| 4,463,045 A | 7/1984 | Ahr et al. |
| 4,509,908 A | 4/1985 | Mullane, Jr. |
| 4,515,168 A | 5/1985 | Chester et al. |
| 4,556,441 A | 12/1985 | Faasse, Jr. |
| 4,585,991 A | 4/1986 | Reid et al. |
| 4,597,961 A | 7/1986 | Etscorn |
| 4,609,518 A | 9/1986 | Curro et al. |
| 4,630,603 A | 12/1986 | Greenway |
| 4,743,249 A | 5/1988 | Loveland |
| 4,784,737 A | 11/1988 | Ray et al. |
| 4,812,305 A | 3/1989 | Vocal |
| 4,837,049 A | 6/1989 | Byers et al. |
| 4,846,821 A | 7/1989 | Lyons et al. |
| 4,904,475 A | 2/1990 | Gale et al. |
| 4,966,159 A | 10/1990 | Maganias |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,190,558 A | 3/1993 | Ito |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabineau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Ericksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,873,849 A | 2/1999 | Bernard |
| 5,879,326 A | 3/1999 | Godshall et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | Devillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kliener et al. |
| 6,379,324 B1 | 4/2002 | Garstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |

(56) References Cited

U.S. PATENT DOCUMENTS

| | | | |
|---|---|---|---|
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whitson |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 7,011,844 B2 | 3/2006 | Gale et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,572,405 B2 | 8/2009 | Sherman et al. |
| 7,578,954 B2 | 8/2009 | Gartstein et al. |
| 7,611,481 B2 | 11/2009 | Cleary et al. |
| 7,763,203 B2 | 7/2010 | Arias et al. |
| 2001/0023324 A1 | 9/2001 | Pronovost et al. |
| 2001/0023351 A1 | 9/2001 | Eilers et al. |
| 2002/0006355 A1 | 1/2002 | Whitson |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0193729 A1 | 12/2002 | Cormier et al. |
| 2002/0193819 A1 | 12/2002 | Porter et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0195474 A1 | 10/2003 | Down et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0062813 A1 | 4/2004 | Cormier et al. |
| 2004/0087992 A1 | 5/2004 | Gartstein et al. |
| 2004/0096455 A1 | 5/2004 | Maa et al. |
| 2004/0106904 A1 | 6/2004 | Gonnelli et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho |
| 2004/0204669 A1 | 10/2004 | Hofmann |
| 2004/0220535 A1 | 11/2004 | Canham |
| 2004/0236271 A1 | 11/2004 | Theeuwes et al. |
| 2004/0265365 A1 | 12/2004 | Daddona et al. |
| 2005/0049549 A1* | 3/2005 | Wong et al. .......... 604/46 |
| 2005/0089554 A1 | 4/2005 | Cormier et al. |
| 2005/0096586 A1 | 5/2005 | Trautman et al. |
| 2005/0163827 A1 | 7/2005 | Zech et al. |
| 2005/0178760 A1 | 8/2005 | Chang et al. |
| 2005/0197308 A1 | 9/2005 | Dalton |
| 2005/0209565 A1 | 9/2005 | Yuzhakov et al. |
| 2005/0228340 A1 | 10/2005 | Cleary et al. |
| 2006/0024358 A1 | 2/2006 | Santini et al. |
| 2006/0076718 A1 | 4/2006 | Sherman et al. |
| 2006/0095061 A1 | 5/2006 | Trautman et al. |
| 2006/0129174 A1 | 6/2006 | Gartstein et al. |
| 2007/0027427 A1 | 2/2007 | Trautman et al. |
| 2007/0191761 A1 | 8/2007 | Boone et al. |
| 2008/0114298 A1 | 5/2008 | Cantor et al. |
| 2008/0183144 A1 | 7/2008 | Trautman et al. |
| 2008/0195035 A1 | 8/2008 | Fredrickson et al. |
| 2008/0269685 A1 | 10/2008 | Singh et al. |
| 2009/0017210 A1* | 1/2009 | Andrianov et al. .......... 427/256 |
| 2009/0155330 A1 | 6/2009 | Ghartey-Tagoe et al. |
| 2010/0028390 A1 | 2/2010 | Cleary et al. |

FOREIGN PATENT DOCUMENTS

| | | |
|---|---|---|
| CA | 2422907 | 4/2002 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0312662 | 4/1989 |
| EP | 0400249 | 12/1990 |
| EP | 0407063 | 1/1991 |
| EP | 0796128 | 9/1997 |
| EP | 1086718 A1 | 3/2001 |
| EP | 1086719 | 3/2001 |
| EP | 1174078 | 1/2002 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |

(56) References Cited

FOREIGN PATENT DOCUMENTS

| | | |
|---|---|---|
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| SU | 1641346 | 4/1991 |
| SU | 1667864 | 8/1991 |
| WO | WO 93/15701 | 8/1993 |
| WO | WO 93/17754 | 9/1993 |
| WO | WO 94/23777 | 10/1994 |
| WO | WO 95/22612 | 8/1995 |
| WO | WO 95/33612 | 12/1995 |
| WO | WO 96/00109 | 4/1996 |
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/13544 | 4/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/28307 | 7/1998 |
| WO | WO 99/00155 | 1/1999 |
| WO | WO 99/29298 | 6/1999 |
| WO | WO 99/29364 | 6/1999 |
| WO | WO 99/29365 | 6/1999 |
| WO | WO 99/61888 | 12/1999 |
| WO | WO 99/64580 | 12/1999 |
| WO | WO 00/05166 | 2/2000 |
| WO | WO 00/35530 | 6/2000 |
| WO | WO 00/70406 | 11/2000 |
| WO | WO 00/74763 | 12/2000 |
| WO | WO 00/74764 | 12/2000 |
| WO | WO 00/74765 | 12/2000 |
| WO | WO 00/74766 | 12/2000 |
| WO | WO 00/77571 | 12/2000 |
| WO | WO 01/08242 | 2/2001 |
| WO | WO 01/36037 | 5/2001 |
| WO | WO 01/36321 | 5/2001 |
| WO | WO 01/49362 | 7/2001 |
| WO | WO 02/02180 | 1/2002 |
| WO | WO 02/07543 | 1/2002 |
| WO | WO 02/07813 | 1/2002 |
| WO | WO 02/17985 | 3/2002 |
| WO | WO 02/32331 | 4/2002 |
| WO | WO 02/32480 | 4/2002 |
| WO | WO 02/062202 | 8/2002 |
| WO | WO 02/072189 | 9/2002 |
| WO | WO 02/091922 | 11/2002 |
| WO | WO 02/100474 | 12/2002 |
| WO | WO 03/024290 | 3/2003 |
| WO | WO 03/024518 | 3/2003 |
| WO | WO 03/026733 A2 | 4/2003 |
| WO | WO 2004/076339 | 9/2004 |
| WO | WO 2004/110717 | 12/2004 |
| WO | WO 2005/082596 A1 | 9/2005 |
| WO | WO 2005/094526 | 10/2005 |
| WO | WO 2006/020842 | 2/2006 |
| WO | WO 2006/055795 | 5/2006 |
| WO | WO 2007/002523 | 1/2007 |
| WO | WO 2007/075806 A2 | 7/2007 |
| WO | WO 2007/124411 | 11/2007 |
| WO | WO 2008/011625 | 1/2008 |
| WO | WO 2008/091602 | 7/2008 |
| WO | WO 2008/130587 | 10/2008 |
| WO | WO 2009/048607 A1 | 4/2009 |
| WO | WO 2009/054988 A1 | 4/2009 |

OTHER PUBLICATIONS

Henry, et al., "Micromachined microneedles for transdermal delivery of drugs", IEEE Workshop on Micro Electro Mechanical Systems, New York, NY, pp. 494-498, (1998).

Henry, et al., "Microfabricated microneedles: A novel approach to transdermal drug delivery", J. Pharmaceutical Science. vol. 87, No. 8, pp. 922-925, (1998).

"Heparin Pregnancy and Breast Feeding Warnings". Drugs.com, Accessed Oct. 8, 2009, <http://www.drugs.com/pregnancy/heparin.html>.

International Search Report from PCT/US2000/015612 mailed on Sep. 7, 2000.

International Search Report from PCT/US2000/015613 mailed on Sep. 6, 2000.

International Search Report from PCT/US2000/015614 mailed on Sep. 6, 2000.

International Search Report from PCT/US2001/031977 mailed on Apr. 29, 2002.

International Search Report from PCT/US2001/031978 mailed on Apr. 29, 2002.

International Search Report from PCT/US2002/014624 mailed on Sep. 3, 2002.

International Search Report from PCT/US2002/029228 mailed on Apr. 23, 2003.

International Search Report from PCT/US2002/029245 mailed on Dec. 27, 2002.

International Search Report from PCT/US2004/005382 mailed on Nov. 25, 2004.

International Search Report from PCT/US2004/017255 mailed on May 24, 2005.

International Search Report from PCT/US2005/009854 mailed on Jul. 3, 2008.

International Search Report from PCT/US2008/000824 mailed on Jul. 18, 2008.

International Search Report from PCT/US2008/004943 mailed on Jun. 9, 2009.

International Search Report from PCT/US2008/011635 mailed on Dec. 19, 2008.

Matriano, et al., "Macroflux(R) microprojection array patch technology: A new and efficient approach for intracutaneous immunization", Pharm. Res., vol. 19, No. 1, pp. 63-70, (2002).

McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.

Mikszta, et al., "Improvred genetic immunization via micromechanical disruption of skin-barrier function and targeted epidermal delivery", Nat. Med., vol. 8, No. 4, pp. 415-419, (2002).

Mikszta, et al., "Protective immunization against inhalation anthrax: A comparison of minimally invasive delivery platforms", J. Inf. Dis., vol. 191, No. 2, pp. 278-288. (2005).

Papautsky, et al., "Micromachined Pipette Arrays," MPA, Proceedings—19th international Conference—IEEE/EMBS, Chicago IL, USA, pp. 2281-2284 (1997).

Park, et al. "Polymer Microneedles for Controlled-Release Drug Delivery," Pharmaceutical Research, Kluwer Academic Publishers-Plenum Publishers, NE, vol. 23, No. 5, pp. 1008-1019 (2006).

(56) References Cited

OTHER PUBLICATIONS

Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, *Therapeutic Protein and Peptide Formulation and Delivery*, American Chemical Society, Washington DC, Chapter 8, pp. 124-153, (1997).
Rydberg, et al., "Low-molecular-weight heparin preventing and treating DVT", Am. Fam. Physician, vol. 59, No. 6, pp. 1607-1612, (1999).
Sivamani, et al., "Microneedles and transdermal applications", Exp. Opin. Drug Del., vol. 4, No. 1, pp. 19-25, (2007).
Wouters, et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography", Annu. Rev. Mater. Sci., vol. 28, pp. 153-184 (1998).

\* cited by examiner

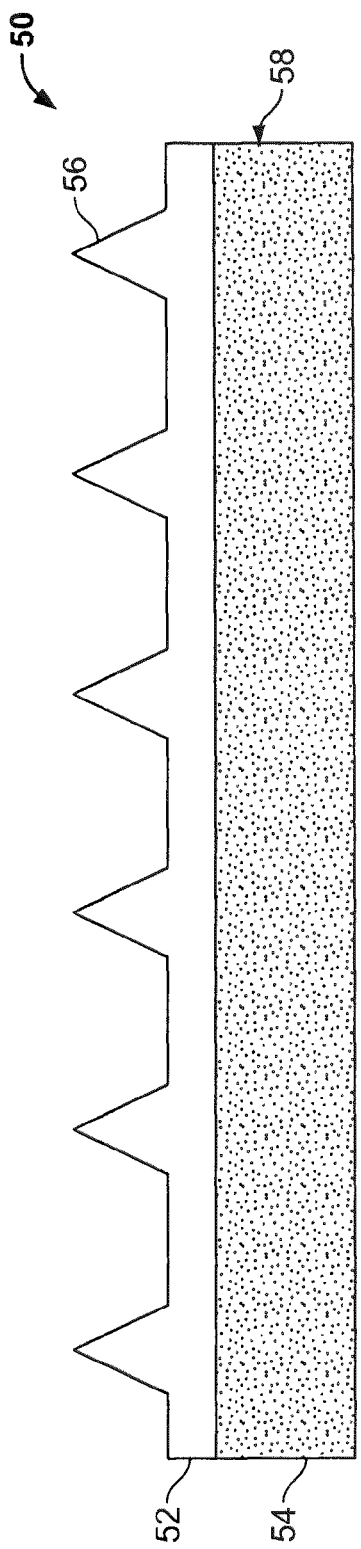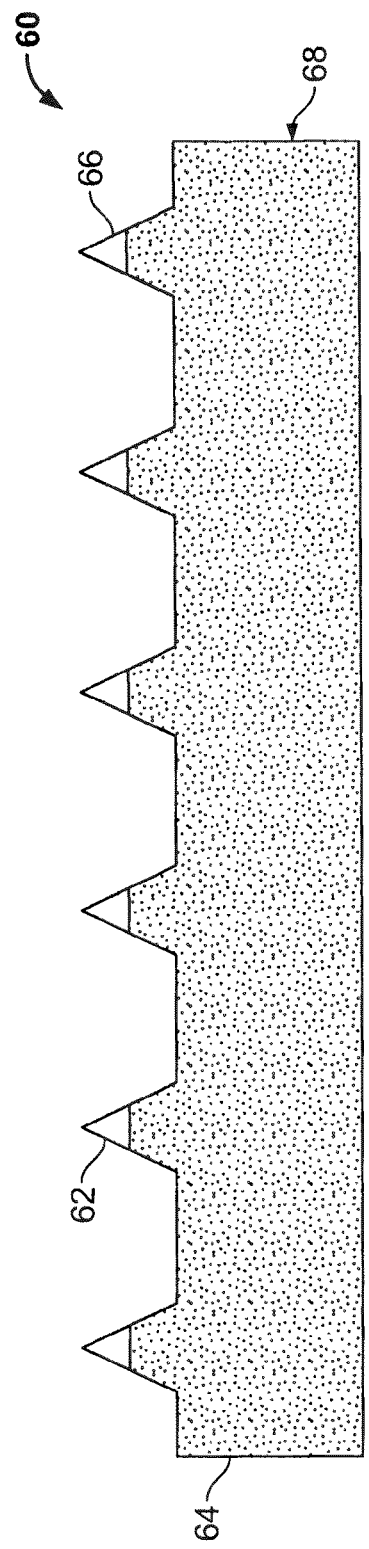
FIG. 9A
FIG. 9B

METHOD AND DEVICE FOR TRANSDERMAL DELIVERY OF PARATHYROID HORMONE USING A MICROPROJECTION ARRAY

CROSS-REFERENCE TO RELATED APPLICATIONS

This application claims the benefit of U.S. Provisional Application No. 61/331,226, filed May 4, 2010, which is incorporated by reference herein.

TECHNICAL FIELD

This disclosure relates generally to a method and drug delivery system for transdermally administering parathyroid hormone (PTH) using an array of microprojections, and related features thereof.

BACKGROUND

Human parathyroid hormone (hPTH) is an 84 amino acid protein that is secreted by the parathyroid gland; PTH is involved in calcium and phosphorus homeostasis and the control of bone growth and density. Two forms of recombinant hPTH have been evaluated in clinical trials, hPTH(1-34) and the full length 84-amino acid, hPTH(1-84). hPTH(1-34) is an N-terminal fragment of PTH, which, along with fragment 1-38, retains the full biological activity of the intact protein.

A recombinant, rDNA-derived, injectable form of hPTH(1-34) (teriparatide) was approved in the United States in 2002 for the treatment of severe osteoporosis and is sold under the tradename FORTEO® (Eli Lilly), referred to hereafter as subcutaneously injected teriparatide. The subcutaneously injected teriparatide is typically prescribed for women with a history of osteoporotic fracture, those having multiple risk factors for fracture, or who have failed or are intolerant of other osteoporosis therapies. In postmenopausal women, subcutaneously injected teriparatide has been found to increase bone mineral density and reduce the risk of vertebral and non-vertebral fractures. Subcutaneously injected teriparatide has also been described to increase bone mass in men with primary or hypogonadal osteoporosis who are at a high risk for fracture. In men with primary or hypogonadal osteoporosis, subcutaneously injected teriparatide has similarly been reported to increase bone mineral density. In 2009, subcutaneously injected teriparatide was also approved for treatment of osteoporosis in men and women associated with sustained systemic glucocorticoid therapy at high risk for fracture.

Bone degenerative diseases such as osteoporosis occur in a substantial portion of the senior adult population. Osteoporosis encompasses a heterogeneous group of disorders that represent a major risk for bone fractures, and a substantial burden on the health care system. Billions of dollars are spent annually on medical care for the treatment of osteoporosis. Clinically, osteoporosis is characterized by diminished bone mass, decreased bone mineral density (BMD) and bone mineral content (BMC), and loss of bone architecture resulting in decreased bone strength and increased risk of bone fracture.

While a number of antiresorptive agents including calcitonin, bisphosphonates, estrogen, and selective estrogen receptor modulators (SERMs) prevent further bone loss, they do not rebuild bone once it has been lost. This is in contrast to subcutaneously injected teriparatide, which represents the first-FDA approved anabolic bone building agent for the treatment of osteoporosis. PTH or PTH(1-34) is thought to exert its effects through receptor-mediated activation of two intracellular signaling pathways via (1) adenylate cyclase and protein kinase A, and (2) phospholipase C and protein kinase C. PTH(1-34) builds bone mass, restores bone architecture, and reduces the risk of vertebral and non-vertebral bone fractures in osteoporotic patients who are at high risk of fracture (R. Neer, *NEJM,* 344:1434, 2001).

As a peptide product, PTH(1-34) requires daily subcutaneous injections an administration regime that is less than ideal. Indeed, most patients have an aversion to self-injection of drugs, and the need to visit a clinic or doctor's office for administration is inconvenient and burdensome. Moreover, severely osteoporotic patients may be unable to self-administer such injections, such that each of the foregoing factors can contribute to poor patient compliance.

While other forms of administration have been suggested, such as oral delivery to the stomach, transdermal delivery, and nasopharyngeal absorption, none of these delivery routes has been proven to be particularly effective and each suffers from certain drawbacks. Oral delivery results in very low bioavailability of polypeptide drugs, usually below 1%, due to degradation in the gastrointestinal tract. Moreover, the epithelial lining of the gastrointestinal tract is impermeable to most polypeptides. Nasopharyngeal and passive transdermal delivery avoid the problems of enzyme degradation, but usually require penetration enhancers in order to effect systemic absorption. Even with such penetration enhancers, bioavailability will usually be very low, and the penetration enhancers can often cause undesirable irritation. In the case of nasopharyngeal administration, penetration enhancers can often damage the nasal epithelium and chronic use has been associated with hyperplasia of the nasal lining.

It is presently believed that PTH is most effectively delivered to a patient in a pulsatile fashion to achieve active bone formation. That is to say, plasma concentrations of PTH should ideally rise rapidly after administration (rapid onset) and fall rapidly after a peak has been reached (rapid decline), generally resulting in a spike in the plasma concentration profile. Thus, a particularly desirable method of administration of PTH is one that achieves such a plasma concentration profile.

For at least these reasons, it would be desirable to provide an alternative delivery method for parathyroid hormone which is patient acceptable. Any such method should avoid subcutaneous injection, limit irritation to the skin and body mucosa, and provide a desired pulsatile delivery profile as described above, among having other advantageous features. Such method should ideally provide for high levels of PTH bioavailability, be amenable to self-administration by the patient, be minimally invasive, and ideally provide a pharmacokinetic profile that is similar to, or preferably improved over, that achieved upon subcutaneous administration.

BRIEF SUMMARY

The present disclosure is directed generally to a device and method of transdermally administering PTH, inclusive of PTH analogs, fragments, salts, etc., in a pulsatile fashion to a mammalian subject, where the method results in pharmacokinetics and a related delivery profile that are surprisingly superior to subcutaneously administered PTH, particularly with respect to the rapid pharmacokinetics achieved.

Additional advantageous features achieved by the device and methods of the invention are described in greater detail herein.

In a first aspect, provided herein is a method of transdermally administering PTH in a pulsatile fashion to a mammalian subject. The method comprises applying to a skin site of a subject a microprotrusion array comprising a plurality of microprotrusions extending from an approximately planar base, each microprotrusion comprising an end portion distal to the base and an upper portion proximal to the base, at least the end portion comprising parathyroid hormone (PTH) in a water-soluble polymer matrix; inserting all or a portion of the plurality of microprotrusions into the skin, and maintaining the array on the skin site for 15 minutes or less, whereby at least a portion of the end portions of the plurality of microprotrusions detach from the microprotrusion array; and whereby the method achieves an average time to maximum PTH plasma concentration ($T_{max}$) of about ten minutes or less.

In one embodiment, the PTH is human parathyroid hormone (1-34).

In yet another embodiment, the microprotrusion array comprises from about 1500 to about 3200 microprotrusions, more preferably from about 2200 to about 3200 microprotrusions.

In yet a further embodiment, the microprotrusion array possesses a diameter ranging from about 8 millimeters to about 14 millimeters.

In yet an additional embodiment related to any one or more of the foregoing, the water-soluble matrix comprises dextran and sorbitol, along with additional optional excipients. For example, in a further embodiment, the water-soluble matrix further comprises histidine and histidine hydrochloride.

In a further embodiment, the microprotrusions themselves comprise PTH in a water-soluble polymer matrix, rather than having PTH present as a coating on the microprotrusions. That is, the PTH is admixed with and/or incorporated into the water-soluble polymer matrix from which at least the tip portions of each microprojection is formed.

In yet another embodiment of the method, the water-insoluble polymer comprises poly(lactic acid-co-glycolic acid).

In a further embodiment of the method, the base and the upper portion of the microprotrusion array comprise the same water-insoluble polymer.

In yet another embodiment related to the foregoing, the base and the upper portion of the microprotrusion array comprise the same material.

In a further embodiment, the end portion and the upper portion of each microprotrusion in the microprotrusion array are composed of a water-insoluble polymer material that dissolves or biodegrades after insertion into the skin.

In another embodiment, the microprotrusion array comprises a dose of PTH, and at least about 80% of the dose is disposed in the end portions of the microprotrusions in the array.

In another embodiment of the method, the array is maintained on the skin site for no more than about 10 minutes, alternatively for about 10 minutes or less, alternatively for a time between 1 second and 10 minutes, inclusive, or between 5 seconds, 10 seconds, 15 seconds and 10 minutes.

In yet another embodiment, the array is maintained on the skin site for no more than about 5 minutes, alternatively for about 5 minutes or less.

In yet an additional embodiment, the method is effective to deliver at least about 55 percent of the total dose of PTH in the array to the subject. In another embodiment, the method is effective to deliver at least about 60 percent of the total dose of PTH in the array to the subject, more preferably at least about 65 percent of the total PTH dose in the array, based on a residual analysis of the device.

In yet another embodiment, the microprotrusion array is applied to the abdomen of the subject.

In yet a further embodiment, the method achieves an elimination half-life ($t_{1/2}$) of PTH that is at least about 15%, 20%, 22% 25% or 30% lower than the elimination half-life ($t_{1/2}$) of the same dose of PTH administered subcutaneously.

In a second aspect, provided herein is a microprojection array for use in delivering hPTH in accord with the delivery parameters as described in any one or more of the foregoing embodiments.

In yet a third aspect, a kit comprising (i) a microprotrusion array comprised of a plurality of microprotrusions extending from an approximately planar base, each microprotrusion comprising an end portion distal to the base and an upper portion proximal to the base, the end portion of each microprotrusion comprising PTH in a water-soluble polymer matrix, said array comprising a therapeutically effective amount of PTH, and (ii) an applicator-assembly to which the microprotrusion array is insertable or affixable or in another embodiment, (ii) an applicator to which the microprotrusion array is insertable or affixable, is provided.

In one embodiment, the microprotrusion array is provided in the kit secured to a support or holding member, such as a plunger, that is insertable into the applicator assembly.

In another embodiment of the third aspect, the kit further comprises an applicator assembly comprising a housing in which the array support member and microprotrusion array can be disposed, and an energy-storage member that, in one embodiment, is movable between first and second stable configurations.

In one or more related embodiments, the kit comprises a microprotrusion array according to one or more of the array embodiments described herein.

In yet another embodiment, the applicator assembly further comprises fasteners to temporarily connect the housing and the energy storage member prior to assembly.

In a more specific embodiment of the kit, the applicator assembly is packaged in a first package or protective container.

In yet another embodiment of the kit, the microprotrusion array and an array support member are packaged together in a second package or protective container.

In a further embodiment, the kit comprises (i) a packaged applicator assembly and (ii) a packaged microprotrusion array and array support member that is insertable into the applicator assembly prior to use.

Additional embodiments of the present method, microprojection array, kit, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

These and other objects and features of the invention will become more fully apparent when read in conjunction with the following detailed description.

BRIEF DESCRIPTION OF THE FIGURES

FIGS. 9A-9B depict schematically in cross-section exemplary microprojection arrays.

DETAILED DESCRIPTION

Figure 1:
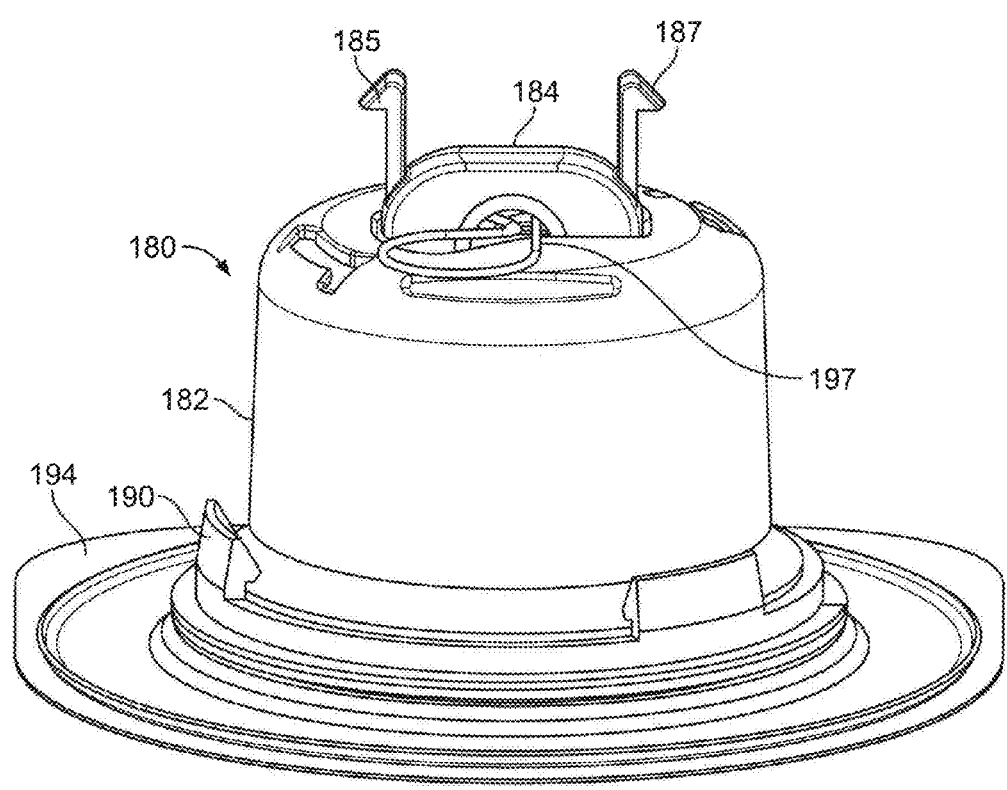
FIG. 1 demonstrates a fully assembled applicator.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon. Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

Definitions

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

In describing and claiming the present invention, the following terminology will be used in accordance with the definitions described below.

"Pulsatile delivery" or delivery in a pulsatile fashion refers to a rapid rise in blood plasma concentration of drug such as PTH after administration, followed by a rapid decline of blood plasma concentration of drug following attainment of Cmax (i.e., generally characterized by a "spike" in the concentration profile).

"Transdermal" refers to the delivery of an agent such as PTH into and/or through the skin for local or systemic therapy.

Reference to a "PTH", or a PTH-agent or to "hPTH(1-34)", as used herein, is meant to include, without limitation, hPTH(1-34), hPTH salts, teriparatide, and the like, including recombinant hPTH(1-34), synthetic hPTH(1-34), and simple known derivatives of hPTH(1-34), such as hPTH(1-34) amide. Examples of hPTH salts include, without limitation, salts having counter-ions such as acetate, propionate, butyrate, pentanoate, hexanoate, heptanoate, levulinate, chloride, bromide, citrate, succinate, maleate, glycolate, gluconate, glucuronate, 3-hydroxyisobutyrate, tricarballylicate, malonate, adipate, citraconate, glutarate, itaconate, mesaconate, citramalate, dimethylolpropinate, tiglicate, glycerate, methacrylate, isocrotonate, beta-hydroxibutyrate, crotonate, angelate, hydracrylate, ascorbate, aspartate, glutamate, 2-hydroxyisobutyrate, lactate, malate, pyruvate, fumarate, tartarate, nitrate, phosphate, benzene, sulfonate, methane sulfonate, sulfate and sulfonate. A PTH-agent as described herein is meant to include any and all forms thereof, including free base and acid forms, charged or uncharged forms, stereoisomers, chiral forms, and the like.

The terms "microprotrusion", "microprojection" or "microneedle" are used herein to refer to elements adapted to penetrate or pierce the stratum corneum or other biological membranes. For example, illustrative microprotrusions or microprojections may include, in addition to those provided herein, microblades as described in U.S. Pat. No. 6,219,574 and Canadian Patent Application No. 2,226,718, edged microneedles as described in U.S. Pat. No. 6,652,478, and microprotrusions as described in US Patent Publication No. US 2008/0269685.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

A material that is "water-soluble" such as the polymer matrix described herein, is dissolvable at physiological pH, such that the material dissolves into or within the skin.

Overview

As described above, provided herein is a method and drug delivery system for transdermally administering parathyroid hormone (PTH) using an array of microprojections. The method and related drug delivery system provides several unexpected advantages over subcutaneous administration, in particular with the pharmacokinetic profile achieved, especially its rapid on-set to Cmax and subsequent rapid elimination rate, thus permitting a pulsed delivery profile. The method, exemplary microprojection arrays, and related features will now be described in greater detail below.

MicroProjection Array

General features of a microprojection array for use in the instant method are described in detail in U.S. Patent Publication No. US 2008/0269685, the entire content of which is explicitly incorporated herein by reference, and described more fully below. See, in particular. FIGS. 3, 4, 5A, 5B, 5C and 6.

In reference to the microprojections themselves, in general, the microprojections have a height of at least about 100 µm, or at least about 150 µm, or at least about 200 µm, or at least about 250 µm, or at least about 300 µm. In general, the microprojections have a height of no more than about 1 mm, no more than about 500 µm, no more than about 300 µm, or in some cases no more than about 200 µm or 150 µm. The microprojections may have an aspect ratio (height to diameter at base) of at least 10:1, preferably at least about 5:1, more preferably at least about 3:1, or at least about 2:1, or at least about 1:1. An illustrative shape for the microprojections is a cone with a polygonal bottom, for example, being hexagonal or rhombus-shaped. Additional microprojection shapes include those provided, for example, in U.S. Patent Publication No. 2004/0087992. While the array itself may possess any of a number of shapes, the array is generally sized to possess a diameter of from about 5 millimeters to about 25 millimeters, or from about 7 to about 20 millimeters, or from about 8 to about 14 millimeters. Exemplary diameters include 5, 6, 7, 8, 9, 10, 11, 12, 13, 14, 15, 18, 17, 18, 19, 20, 21, 22, 23, 24, and 25 millimeters.

The microprojections may in some cases have a shape which becomes thicker towards the base, for example microprojections which have roughly the appearance of a funnel, or more generally where the diameter of the microprojection grows in a faster than linear fashion with respect to distance to the microprojection's distal end. Such a shape may, for example, facilitate drug loading. Where microprojections are thicker towards the base, a portion of the microprojection adjacent to the base, which may be referred to herein as a "backing portion" or 'foundation' or as an "upper portion" may be designed not to penetrate the skin.

Generally, the number of microprotrusions in the array is preferably at least about 100, at least about 500, at least about 1000, at least about 1400, at least about 1600, or at least about 2000. For example, the number of microprotrusions in the array may range from about 1000 to about 4000, or from about 2000 to about 4000, or from about 2000 to about 3500, or from about 2200 to about 3200. The area density of microprotrusions, given their small size, may not be particularly high, but for example the number of microprotrusions per $cm^2$ may be at least about 50, at least about 250, at least about 500, at least about 750, at least about 1000, or at least about 1500. An illustrative microprotrusion array is described herein in Examples 9-11.

Examples of forming various microprotrusion arrays having different configurations are provided in Examples 1-7. Generally, an array is prepared by (a) providing a mold with cavities corresponding to the negative of the microprotrusions, (b) filling the mold with a casting solution comprising a biocompatible material such as a biocompatible polymer and a solvent, (c) removing the solvent, and (d) demolding the resulting array from the mold. The solution preferably contains an active ingredient such as PTH. In one or more embodiments, the microprojections themselves comprise PTH in a water-soluble polymer matrix, as opposed to having the PTH present as a coating on a microprojection or microneedle made of a different, biocompatible material such as a metal.

The molds can be made using a variety of methods and materials. Materials for forming a mold include ceramic materials, silicone rubbers, polyurethanes, and waxes. A exemplary silicone rubber system is the Sylgard® system from Dow Corning (Midland, Mich.), for example Sylgard® 184. Nusil MED 6215, 6210 is an alternative system available from NuSil Technology (Carpinteria, Calif.).

The molds can be prepared by any of a number of methods including casting the liquid mold material over a master microneedle array and allowing the material to dry and solidfy by curing the liquid mold material over a master microneedle array so it solidifies, such curing being affected by temperature or other means, by heating the mold material until it melts, followed by casting the melted liquid over microarray, and allowing the material to cool and solidify, or by pressing the master microneedle array into the mold material. The molds can also be made by plating metal (such as nickel, copper or gold) onto a master microneedle array.

The solution which is cast preferably comprises one or more polymers in a solvent and an active ingredient (i.e., PTH). The polymers should be biocompatible, in some cases, biodegradable. By this term is meant that a polymer will degrade under expected conditions of in vivo use (e.g., insertion into skin), irrespective of the mechanism of biodegradation. Exemplary mechanisms of biodegradation include disintegration, dispersion, dissolution, erosion, hydrolysis, and enzymatic degradation. One preferred mechanism of biodegradation is dissolution, where the polymer is water-soluble.

Biocompatible, biodegradable, or bioerodible polymers for use in the instant microprojection arrays include poly (lactic acid) (PLA), poly(glycolic acid) (PGA), poly(lactic acid-co-glycolic acid)s (PLGAs), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), other polysaccharides, polyalcohols, gelatin, alginate, chitosan, hyaluronic acid and its derivatives, collagen and its derivatives, polyurethanes, and copolymers and blends of these polymers. A preferred hydroxyethyl starch has a degree of substitution of in the range of 0-0.9.

The biodegradability or dissolvability of the microprojection array may be facilitated by the inclusion of sugars. Exemplary sugars include dextrose, fructose, galactose, maltose, maltulose, iso-maltulose, mannose, lactose, lactulose, sucrose, and trehalose. Sugar alcohols, for example lactitol, maltitol, sorbitol, and mannitol, may also be employed. Cyclodextrins can also be used advantageously in microneedle arrays, for example α, β, and γ cyclodextrins, for example hydroxypropyl-β-cyclodextrin and methyl-β-cyclodextrin. Sugars and sugar alcohols may also be helpful in stabilization of peptides and proteins and in modifying the mechanical properties of the microprojections by exhibiting a plasticizing-like effect.

An exemplary polymer effective for forming a casting solution to fill in the tips or and portion of the microprojections is the polysaccharide, dextran Dextran 1, Dextran 10, Dextran 20, Dextran 40, Dextran 70, Dextran 75, and mixtures thereof), optionally combined with the sugar alcohol, sorbitol.

A particularly preferred formulation for filling the end portion or tip of the microprojections comprises hPTH(1-34), dextran, and sorbitol. In a preferred embodiment, the PTH is provided in a water-soluble matrix. The water-soluble matrix comprises dexran, sorbitol, and PTH counterion, if contained in the PTH source material. Additional components may include buffers such as histidine and histidine hydrochloride.

The polymers used may possess a variety and range of molecular weights. The polymers may, for example, have molecular weights of at least about 1 KD, at least about 5 kD, at least about 10 kD, at least about 20 kD, at least about 22 kD, at least about 30 kD, at least about 50 kD, or at least about 100 kD.

Exemplary solvents for casting include water, alcohols (for example, $C_2$ to $C_8$ alcohols such as propanol and butanol), and alcohol esters, or mixtures of these. Such solvents are typically useful for casting components which themselves are water-soluble. Other solvents include esters, ethers, ketones, nitriles, lactones, amides, hydrocarbons and their derivatives as well as mixtures thereof.

The mold itself, or portions of it, may be treated to improve wetting using any of a number of well-known surface treatments, such as surfactant coating, salt coating, radiofrequency treatment, plasma treatment and the like.

During solvent removal, the volume of the cast solution will naturally diminish. With an appropriate choice of solvents, it is possible for the distal ends of the microprojections—those furthest from the base—to become finer as a result of solvent removal. Illustrative tip diameters include those of less than about 10 µm, or less than about 5 µm, less than 2 µm, less than about 1.5 µm, or even less than about 1 µm.

The microprotrusion array may be prepared to contain, in addition to PTH, any of a number of different polymers and other additives. Generally, the array comprises an approximately planar base and a plurality of microprotrusions attached thereto. The array typically further contains a plurality (meaning 2 or more) of layers arranged roughly parallel to the plane of the base, where at least two of the plurality of layers comprise different polymers. One layer of the plurality of layers comprises PTH. Optionally, at least one layer of the array or the array housing adheres to human skin.

Various embodiments include the following. For example, compared to the overall volume of the microprojection array, the microprojections themselves may possess a higher amount of PTH. In certain instances, the end portion of the microprojection comprises a higher amount of PTH than the upper portion and/or the base. When the PTH is cast in a water-soluble, dissolvable matrix, the tips or end portions of the microprojections will dissolve more rapidly than other portions of the array, making delivery of drug particularly efficient. Furthermore, in certain treatment protocols, the array may be left on the skin for only a short period of time during which essentially only the microprojections can dissolve to a substantial extent. The desirability of placing a higher amount of active such as PTH in the projections themselves is particularly high when the active is costly. An array configuration that is effective to achieve a high amount of active in the tips or end portions of the microprojections themselves is to load or place a first drug-containing polymer layer in the tips or end portion of the microprojections (or in a substantial portion of the microprojections), and a second polymer layer which includes the upper portion of base or a substantial proportion of the base, but is absent drug (PTH).

FIGS. 9A-9B depict schematically in cross-section two exemplary microprojection arrays suitable for use in the methods described herein. In the first microprojection array shown in FIG. 9A, microprojection array 50 comprises a base 58 and a plurality of microprojections, such as representative microprojection 56. The microprojection array comprises two layers, a first layer 52 and a second layer 54 (shaded). The microprojections, taken in this embodiment to be the portions of the array that extend from the planar surface defined by the proximal skin contacting side of first layer 52, are composed of the material from which first layer 52 is manufactured. In this embodiment, second layer 54 and first layer 52 collectively define the base of the microprojection array, the base having a planar surface from which the microprojections extend. The microprojections extending from layer 52 are comprised of the material from which layer 52 is fabricated. That is, the microprojections are fabricated from a first material and all or a portion of the base is fabricated from the same material. In another embodiment, the microprojections are fabricated from a first material and a portion of the base is fabricated from a different material.

In another embodiment of a microprojection array 60 depicted in FIG. 9B, there are also a plurality of microprojections, such as microprojection 66 which is representative. Each microprojection in the array has an end portion or distal tip 62 that contacts and penetrates (upon application of force) the stratum corneum, and an upper portion proximal the a planar base 64. In this embodiment, the base member and the upper portion of each microprotrusion is comprised of a first material, indicated by the shading in the drawing. The end portion of each microprotrusion is fabricated from a different material. In one embodiment, the material from which the base and upper portions are fabricated is a water-insoluble polymer, and the end portion of each microprotrusion is fabricated from a second or different material that is a water-soluble or dissolvable material. The PTH can be incorporated into only the end portion of each microprotrusion (i.e., "drug-in-tip" as described in some examples) or can be incorporated into the end portion and the upper portion of each microprotrusion. Of course, PTH can also be incorporated into the base, but is normally not for cost of goods and/or safety reasons. In another embodiment, the first material forming the base and upper portion of each microprotrusion, and the material forming the end portion of each microprotrusion are the same polymer material, preferably a dissolvable or biodegradable water soluble polymer, and differ only in that the material forming the end portions contains an active agent such as PTH and the material forming the base and upper portions contain no active agent or a different active agent than the end portions. In one embodiment, at least about 80% of the dose of PTH in the microprotrusion array is confined to the end portion (tip) of each microprotrusion, wherein the "tip" intends that portion of a microprotrusion that is intended to penetrate the stratum corneum. In other embodiments, at least about 85% and at least about 90% or 95% or 98% of the dose of PTH in the microprotrusion array is confined to the end portion (tip) of each microprotrusion.

In one embodiment, to prepare a PTH-containing microarray as provided herein, the solution comprising PTH is cast so that it fills the cavities of a mold. This solution is then dried. A further solution with a lower or zero concentration of active, constituting a second layer, is then cast over the solution or layer comprising the PTH. The polymers used in the first layer are preferably not soluble in the solvent used for the second layer. The second layer preferably uses a different polymer or polymers from the ones used in the first layer. This procedure may produce an array having two layers, and in which the microprojections are enriched in active, in such an array, the active would not be expected to substantially diffuse into the second layer.

The second layer may comprise any of a number of polymers such as cellulose acetate butyrate, cellulose acetate, cellulose acetate propionate, ethyl cellulose, nitrocellulose, hydroxypropyl methyl cellulose phthalate, polystyrene, polyacrylates (such as acrylate/octylacrylamide copolymers, Dermacryl® 97), polymethacrylates (such as Eudragit® E, RL, RS, L100, S100, L100-55), or poly (hydroxyl alkanoates). Preferably the second layer comprises a biocompatible, biodegradable polymer(s) such as PLA, PGA, PLGA, polycaprolactone and copolymers thereof. A particularly preferred polymer is the water-insoluble polymer, PLGA.

Preferably, where the first layer is cast in an aqueous solvent, the second layer comprising the upper portion of the microprojection, and in certain instances, the base, is cast in an organic solvent. Preferred solvents for preparing and casting the second layer include alcohols, for example isopropyl alcohol and ethanol, and esters, for example ethyl acetate, heptane, propyl acetate, or other solvents such as acetonitrile, dimethylsulfone (DMSO), N-methylpyrrolidone (NMP), glycofurol.

As described above, the microprojections of the array preferably detach from the array following insertion into the skin. In one embodiment, only a tip portion of each microprojection detaches from the microarray. In one embodiment, detachment of all of a microprojection or of only a portion of each microprojection is achieved by degradation or dissolution of the material from which that microprojection or that portion of the microprojection is manufactured. Advantages related to this feature include the elimination of sharp disposal requirements, elimination of needle stick injury, and the like.

Detachable microprojections may be prepared using a number of approaches. A layered approach, for example, may be used in which the array is composed of multiple layers, and a layer comprising the attachment areas of the microprojections to the array is more readily degradable or dissolvable than the other layers, such that upon activation, the drug-containing tip of the microprojection is detached from the upper portion of the microprojection or from the base, depending upon the specific configuration. For example, the layer comprising the attachment areas may be more rapidly hydrated than the other layers.

The array may also comprise a polymer or polymer blend having bioadhesive properties which within a certain range of moisture will have higher adhesive strength the greater the moisture. In one embodiment, the multilayer array is one in which the layer or layers in which the microneedles principally lie possess bioadhesive characteristics.

Exemplary polymers with bioadhesive characteristics include suitably plasticized polyvinyl alcohol and polyvinylpyrrolidone. An extensive discussion of a class of bioadhesive polymer blends is found in U.S. Pat. No. 6,576,712 and U.S. Published Patent Applications Nos. 2003/0170308 and 2005/0215727, which are incorporated by reference for their teaching of bioadhesive polymer blends and adhesion testing. Preferable bioadhesive polymers are those which possess hydrogen-bonded crosslinks between strands of the primary polymers. These crosslinks may comprise a comparatively small molecule which forms hydrogen bonds to two primary polymer strands. It is believed that certain sugars may act as a small molecule crosslinker in this manner with particular primary polymers such as polyvinyl alcohol, dextran and tetrastarch.

The microprojection arrays may also include one or more additives or measures to retard or diminish microorganism growth. For example, the microprojection arrays may be packaged in a sealed, low oxygen environment to retard aerobic microorganisms and eventually destroy their viability. The arrays may also be packaged in a low moisture environment to dehydrate microorganisms. Alternatively, a pharmaceutically acceptable antibacterial agent may be included in the formulation or the packaging. Examples of such agents are benzalkonium chloride, benzyl alcohol, chlorbutanol, meta cresol, esters of hydroxyl benzoic acid, phenol, thimerosal, and silver or silver salts. As a further alternative, a surfactant or detergent can be added to the casting formulations to disrupt the cell membrane of potential microorganisms; alternatively, a desiccant may be added to the packaging.

Antioxidants may also be added to the formulation, for example, to protect the PTH from oxidation. Exemplary antioxidants include methionine, cysteine. D-alpha tocopherol acetate, DL-alpha tocopherol, ascorbyl palmitate, ascorbic acid, butylated hydroxyanisole, butylated hydroxyguinone, butylhydroxyanisole, hydroxycomarin, butylated hydroxytoluene, cephalin, ethyl gallate, propyl gallate, octyl gallate, lauryl gallate, propylhydroxybenzoate, trihydroxybutyrophenone, dimethylphenol, ditertbutylphenol, vitamin E, lecithin, and ethanolamine. Chelating agents, e.g. ethylenediaminetetraacetic acid (EDTA), may also be added to the formulation to protect PTH from oxidation.

Formulations

PTH-containing formulations used to prepare the instant microprotrusion arrays are described generally above. The drug-containing formulation, sometimes referred to herein as the drug-in-tip or DIT formulation, contains an amount of PTH sufficient to provide a therapeutically effective amount in the final microprojection array product. Generally, the amount of PTH ranges from about 10-500 µg per dosage unit, or from about 10-250 µg per dosage unit, or from about 10-100 µg per dosage unit.

The PTH is contained in a water-soluble polymer matrix. Preferably, the matrix comprises one or more water-soluble polymers. One preferred water-soluble polymer is a polysaccharide, such as the exemplary polysaccharide, dextran. The dextran preferably possesses a molecular weight ranging from about 1 to about 150 kilodaltons, or from about 40 to about 100 kilodaltons. Representative dextrans possess each of the following molecular weights: 1 kilodaltons, 10 kilodaltons, 20 kilodaltons, 40 kilodaltons, 70 kilodaltons, and 75 kilodaltons. Generally, dextran is present in the final end portion of the microprojections in an amount greater than that of any of the other components. Typically, the amount of polysaccharide, such as dextran 70, ranges from about 1 percent by weight to about 90 percent by weight, more preferably from about 20 percent by weight to about 70 percent by weight, still more preferably from about 35 percent by weight to about 70 percent by weight, of the DIT formulation, based upon dry weight (i.e., the layer after solvent removal). The amount of PTH contained in the layer will of course vary, based upon the amount of PTH to be administered per dosage unit. Generally, the amount contained in the final end portion ranges from about 1 percent by dry weight to about 50 percent by dry weight, more preferably from about 5 percent by dry weight to about 25 percent by dry weight, still more preferably from about 7.5 percent by dry weight to about 10 percent by dry weight. The other major component of the DIT layer is the sugar alcohol, sorbitol. Sorbitol is typically present in an amount less than dextran. Illustrative ranges of sorbitol content are from about 1 percent by weight to about 50 percent by weight, or from about 10 percent by weight to about 35 percent by weight, of the formulation. Thus, the main components forming the water-soluble polymer matrix are PTH, dextran, and sorbitol. Additional lesser components include the buffers histidine and histidine hydrochloride, as well as any PTH counterions, if applicable.

Generally, the casting solutions or precursor solutions to the final DIT layer are prepared to have a total solids content ranging from about 1% solids to about 50% solids, or from 15% solids to about 45% solids, where representative solids contents include 5, 10, 15, 20, 25, 30, 35, 40, 45 and 50% solids.

The upper portion or layer of the microprojections and base typically comprise at least one water-insoluble polymer and are substantially absent PTH, to provide an array having microprojections that are PTH-enriched in comparison to the upper portion and base portions of the array. One preferred type of water-insoluble polymer is PLGA, and in particular, poly(lactic acid-co-glycolic acid), having a lactide to glycolide ratio of 75/25. Materials having other DL-lactide to glycolide ratios may also be used, such as 50:50, 65:35, 85:15, or PLA by itself. Preferably, the PLGA is ester-terminated. Such polymers are available from Durect (Cupertino, Calif.).

Description of an exemplary PTH formulation as described above is provided in Example 9.

Transdermal Delivery Device

In one or more embodiments, the microprojection array forms part of a final transdermal delivery system or product. The product typically comprises the microprotrusion array according to any one or more of the embodiments provided herein, and an array support member (also referred to herein as a microprojection-holding member). The array support member (or microprojection-holding member) is typically affixed or affixable to the base of the microprotrusion array at the surface opposite the microprotrusions. One such exemplary microprojection-holding member is a plunger as described in Example 10.

The product may further comprise an applicator assembly that comprises a housing and an energy storage member effective to activate the device. See, e.g., FIGS. 1 and 2, along with Example 10.

Figure 2:
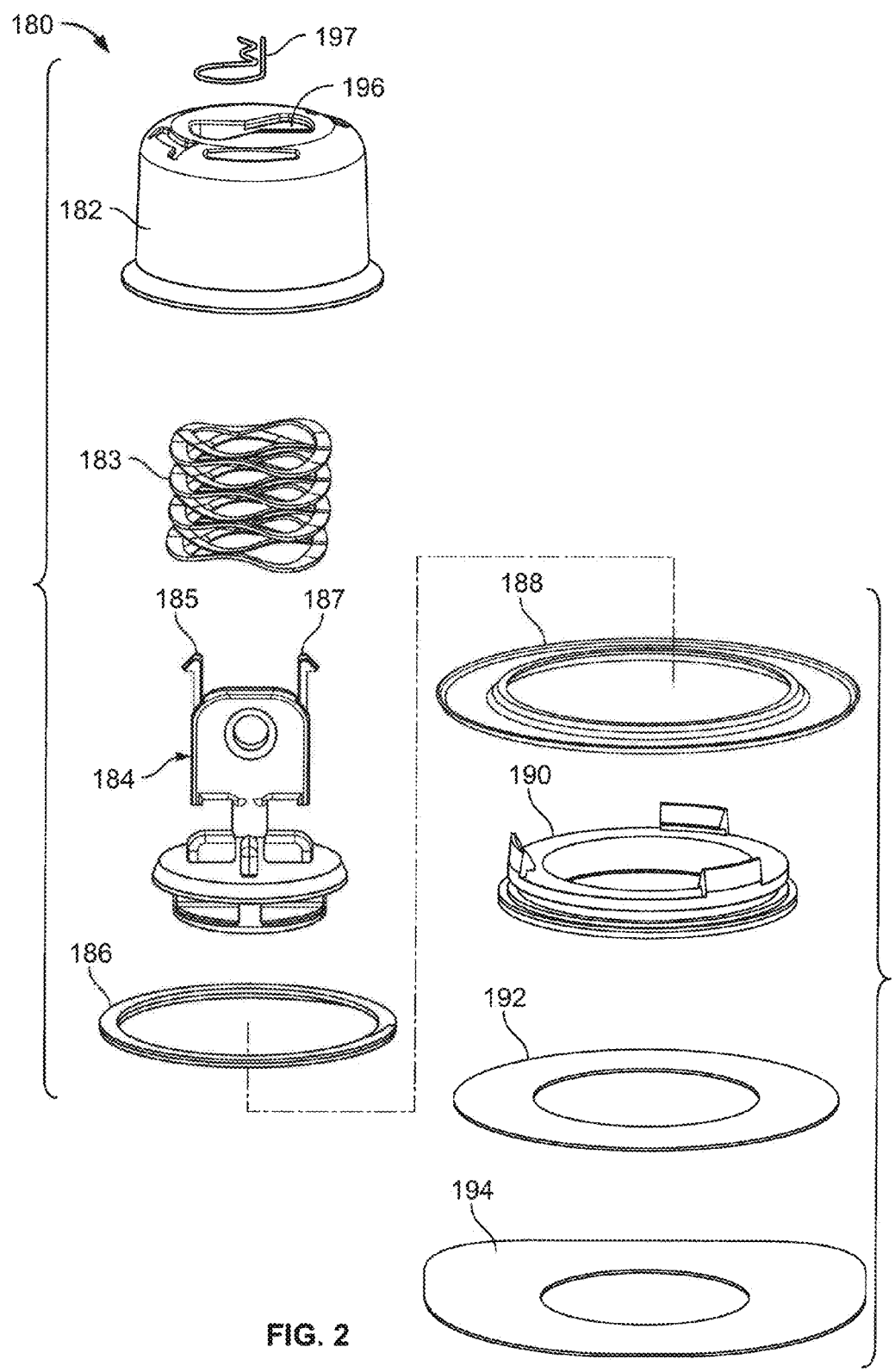
FIG. 2 is demonstrates an exploded view of the applicator of FIG. 1.

As described above, such an applicator suitable for use is illustrated in FIGS. 1 and 2, where an applicator 180 is shown fully assembled in FIG. 1 and in exploded view in FIG. 2. An outer housing 182 is dimensioned to contain an energy-storage member 183 and a microprojection-holding member 184 which holds a microprojection array (not shown in the figures). In storage and prior to use, microprojection-holding member 184 is held in place by two platforms in housing 182, such as platform 196, against which a projection member, such as members 185, 187 in member 184, engages. When it is desired to activate the device, a user twists member 184 (e.g., with thumb and forefingers gripping projection members 185, 187) so that it is no longer over the platforms and restrained by them. When that twisting occurs, energy-storage member 183 moves downward pressing the microprojection-holding member in a downward direction to contact the microprojection array against the skin.

The applicator of FIGS. 1 and 2 is further provided with an optional set of components for adapting to skin, in this case an adapter 190, a snap ring 186, and an extender 188. In addition, FIG. 1 shows an optional adhesive 192 and an optional release liner 194. An optional safety feature to prevent inadvertent or accidental actuation of the applicator can also be provided. In one embodiment, a pin 197 is removably inserted through a cavity in microprojection holding member 184 prior to use. The applicator may be simplified and adapted to reduce the number of parts. To enable the applicator for actuation, a user pulls pin 197 from its retaining position as shown in FIG. 1 to permit a user to activate the applicator by the twisting motion described above. Various configurations, components, and embodiments of a microprojection array-based transdermal delivery system suitable for administering PTH according to the methods provided herein are described in co-owned U.S. Provisional Patent Application No. 60/331,175, filed on May 4, 2010, the entire content of which is expressly incorporated herein by reference. It will be appreciated that the applicator described herein is merely exemplary, and that any applicator that achieves penetration of the microprojections into the skin of a user is contemplated for use in the claimed methods.

Product components may optionally be provided as part of a kit, e.g., for assembly prior to actuation and use, or alternatively, in assembled form. See, e.g., FIG. 1. For example, one such kit may contain a microprojection array along with an array support member, where the array support member is affixable or affixed to the base of the microprotrusion array at the surface opposite the microprotrusions.

The kit may optionally further comprise an applicator assembly comprising a housing in which the array support member and microprotrusion array can be disposed, combined with an energy storage member that is movable between first and second configurations (e.g., a resting position and a position in which the microprojection-holding member is extended in a downward direction to contact the microprojection array against the skin as described above). In one particular embodiment, the energy storage member is a spring. Optionally, the applicator assembly comprises fasteners to temporarily hold together the housing and the energy storage member.

The kit may also comprise various components of the final product as described above to be assembled prior to use, where any of the individual or combinations of components may be provided in primary packaging, and optionally further contained in secondary packaging.

Pharmacokinetics

The microprojection array described herein was used to administer transdermally hPTH(1-34) to healthy human subjects. As a comparator, hPTH(1-34) was also administered subcutaneously to a healthy group of human subjects. Details of this study are provided in Example 11, and the resulting data are presented in FIGS. 3-8 and in Table 1, now to be described.

In this study, a microprojection array was prepared as detailed in Example 9 and inserted into an applicator-array assembly to form a transdermal delivery system, as described in Example 10. The system described in Examples 9 and 10 is referred to herein, and in the drawings, as "MicroCor® hPTH(1-34)" or more simply, "MicroCor®". The delivery system was designed to deliver a systemic dose of hPTH (1-34) across the stratum corneum barrier layer of the skin upon activation of the applicator to deploy an array of microstructures causing the array of microstructures to penetrate the stratum corneum. In this study, two dose levels were administered via the transdermal delivery system. 32 µg hPTH(1-34) and 64 µg hPTH(1-34) (32 µg hPTH(1-34)× 2). Subjects received these doses by applying the transdermal microneedle delivery system MicroCor® device containing the indicated amount of hPTH in the distal tips of the microneedles in the array to an abdominal site, and leaving the device in place for five (5) minutes. The comparator treatment (the commercial hPTH product known as Forteo®) was subcutaneously administered via injection into the abdominal wall at a dose of 20 µg. Blood samples were drawn at designated times and analyzed for hPTH concentration. The pharmacokinetic data is summarized in FIGS. 3-8 and in Table 1.

Figure 3:
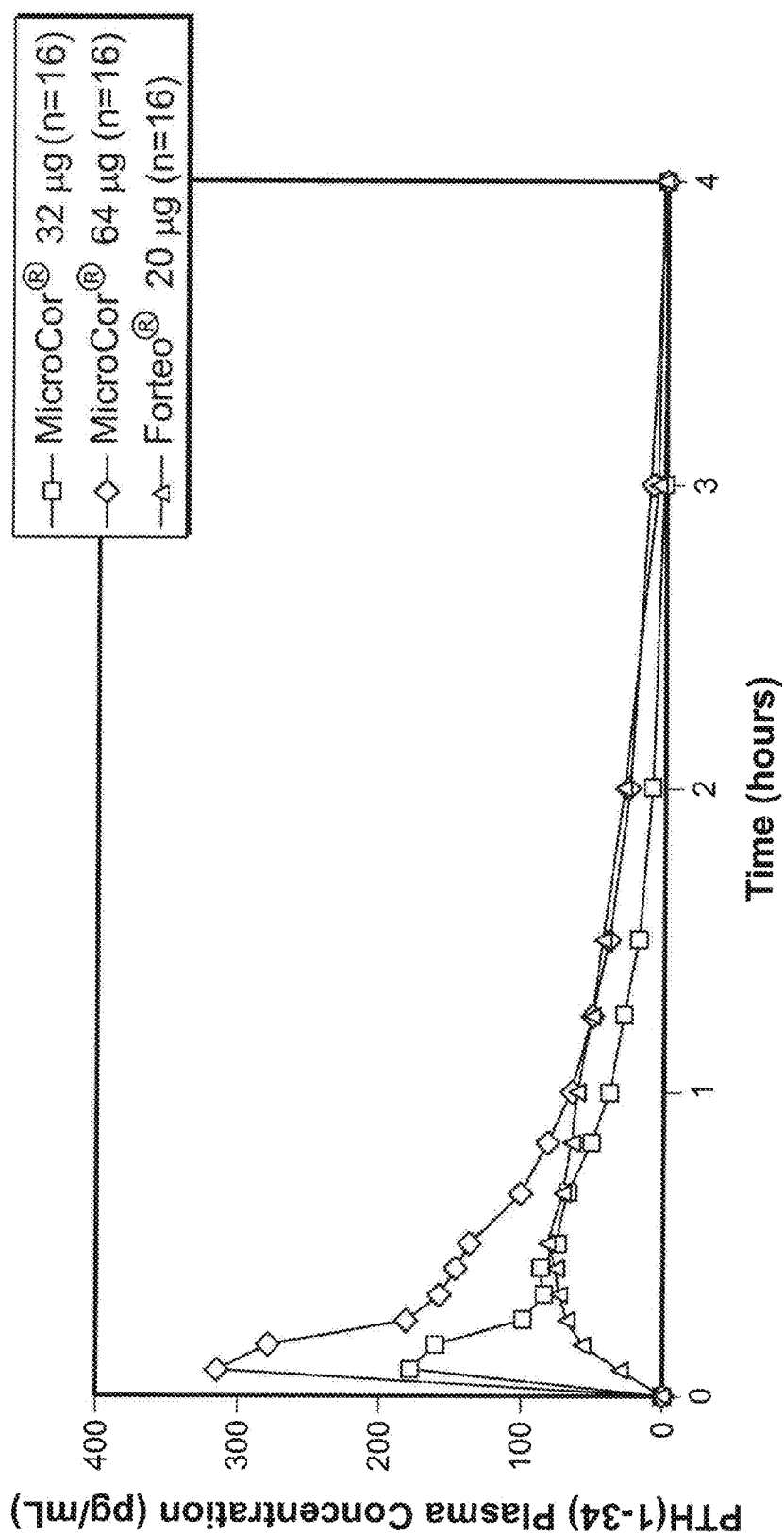
FIG. 3 is a plot of hPTH(1-34) plasma concentration (pg/mL) versus time for an illustrative microprotrusion array-based hPTH transdermal delivery system in comparison to subcutaneous administration of hPTH(1-34) as described in detail in Example 11. Values of maximum plasma concentration and Tmax for the treatments shown are as follows: (transdermal delivery of hPTH via a microprotrusion array known under the tradename MicroCor®, 32 µg: Cmax: 180 µg/mL, Tmax: 8.1 mins; MicroCor® 64 µg: Cmax: 336 pg/mL, Tmax: 7.4 mins; subcutaneously injected teriparatide (Forteo®) 20 µg: Cmax: 85 pg/mL, Tmax: 0.44 mins).

FIG. 3 is a plot of average hPTH(1-34) plasma concentration (µg/mL) versus time, in hours, for subjects treated hPTH administered via the transdermal microneedle delivery system (under the tradename MicroCor®) at a dose of 32 µg (open squares) and 64 µg (open diamonds) or via subcutaneous injection (Forteo®) at a dose of 20 µg (open triangles). Administration of PTH from the microprojection delivery system wherein the PTH was contained within a dissolvable polymer matrix from which the microprojections, or at least the tips of each microprojection, was fabricated, achieved a rapid onset to maximum plasma concentration. Specifically, and with reference to FIGS. 5-6, for the 32 µg dose, a maximum plasma concentration (180 µg/mL) was reached in about 8 minutes, and for the 64 µg dose, a maximum plasma concentration (336 µg/mL) was reached in 7.4 minutes after application of the system to the skin. Subcutaneous injection of a 20 µg dose of PTH, in contrast, achieved its maximum concentration (85 µg/mL) 26 minutes post injection.

Accordingly, in one embodiment, a method for administering PTH to a human subject is provided, by contacting the skin of the subject with a microprotrusion array containing a dose of PTH and causing all or a portion, preferably a majority, of the microprotrusions to penetrate the stratum corneum. Entry of the microprotrusions into the skin achieves delivery of the PTH to the subject, wherein the time to maximum plasma concentration (Tmax) is less than about 20 minutes, more preferably Tmax is achieved in about 15 minutes or less, more preferably in less than about 12 minutes, still more preferably in less than about 10 minutes, more preferably in less than about 9 minutes.

Figure 7:
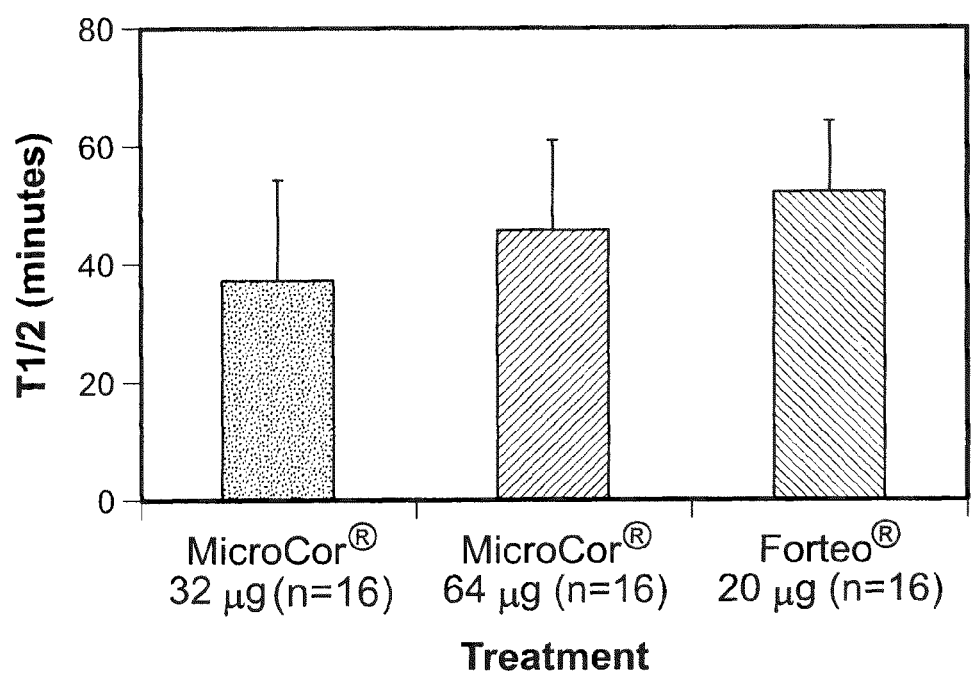
FIG. 7 is a graph illustrating mean T1/2 (minutes) values for each of the three treatment regimes examined: an illustrative microprotrusion array-based hPTH transdermal delivery system (MicroCor® 32 µg dose and MicroCor® 64 µg dose) in comparison to subcutaneous administration (Forteo®, 20 µg dose) as described in detail in Example 11.

With continuing reference to FIG. 3 and additionally to FIG. 7, it can also be seen that administration of PTH from the microprojection delivery system described herein, in addition to a rapid (e.g., about 10 minutes or less) onset to maximum plasma concentration, a rapid elimination rate is also achieved. The elimination half life ($T_{1/2}$), calculated in accord with standard equations and methods in the art and generally reflective of the time for the plasma concentration to fall to half of its original value, was 37 minutes for the 32 µg dose of hPTH administered via the transdermal microneedle delivery system. The elimination half life was 52 minutes for the 20 µg dose of hPTH administered via subcutaneous injection.

Accordingly, in one embodiment, a method for administering PTH to a human subject is provided, by contacting the skin of the subject with a microprotrusion array containing a dose of PTH and causing all or a portion, preferably a majority, of the microprotrusions to penetrate the stratum corneum. Entry of the microprotrusions into the skin achieves delivery of the PTH to the subject, wherein the elimination half life of PTH is less than about 45 minutes, and more preferably is 40 minutes or less. In one embodiment, the PTH when administered via the microneedle delivery system described herein, wherein PTH is contained in a water-soluble polymer matrix in at least the tip portions of each microprojection in an array, provides a time to maximum plasma concentration (Tmax) of less than about 20 minutes, more in about 15 minutes, 12 minutes, 10 minutes or 9 minutes or less, and an elimination half life of less than about 45 minutes, and more preferably 44, 43, 42, 41 or 40 minutes or less.

In another embodiment, PTH administered in accord with the microprotrusion array described herein provides a maximum plasma concentration of greater than about 100 pg/mL, more preferably of 125, 130, 135, 140, 145, 150, 155, 160, 165, 170, or 175 pg/mL, for a dose of 32 µg PTH, in less than about 20 minutes, about 15 minutes, about 12 minutes, about 10 minutes or about 9 minutes, and an elimination half life of less than about 45 minutes, and more preferably 44, 43, 42, 41 or 40 minutes or less.

In another embodiment, a method for administering PTH to a human subject is provided, by contacting the skin of the subject with a microprotrusion array containing a dose of PTH and causing all or a portion, preferably a majority, of the microprotrusions to penetrate the stratum corneum. Entry of the microprotrusions into the skin achieves delivery of the PTH to the subject, wherein the time to maximum plasma concentration (Tmax) is 50% lower (shorter), more preferably 55%, 60%, 65% or 70% less than the time to maximum plasma concentration achieved with the same, or lower dose, of PTH delivered via subcutaneous injection. In another embodiment, the method of PTH administration via a transdermal microneedle array in accord with that described herein provides delivery of PTH to the subject such that the elimination half life is at least about 15%, 20%, 22% or 25% faster than the elimination half life achieved with the same, or lower dose, of PTH delivered via subcutaneous injection.

Figure 4:
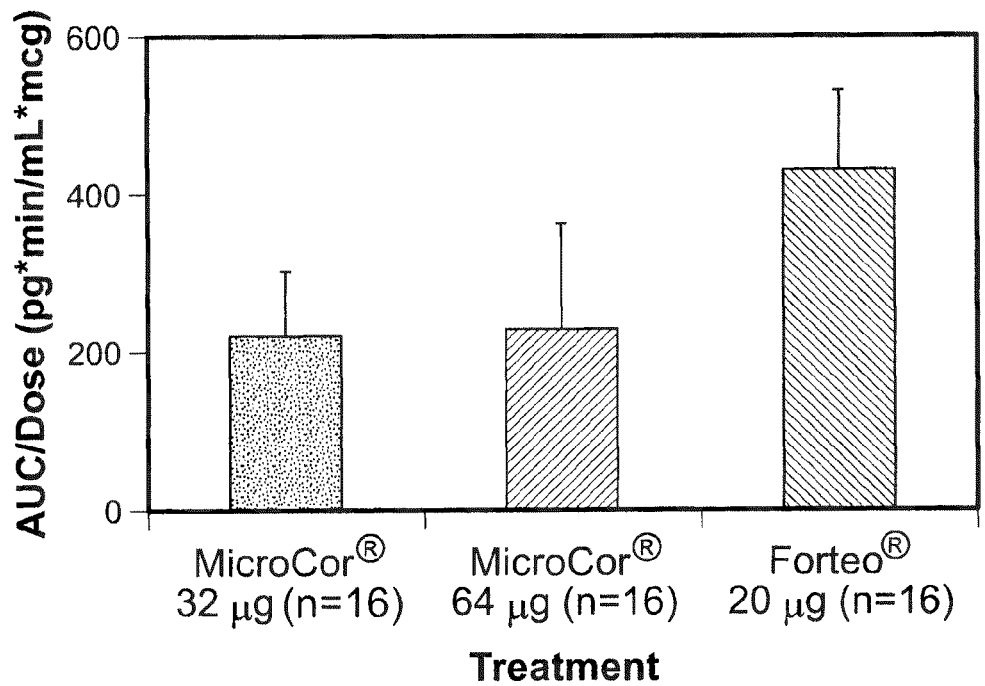
FIG. 4 demonstrates dose-normalized AUC (area under the curve) values (pg*min/mL*µg) for an illustrative microprotrusion array-based hPTH transdermal delivery system in comparison to subcutaneous administration of hPTH as described in detail in Example 11.
Figure 5:
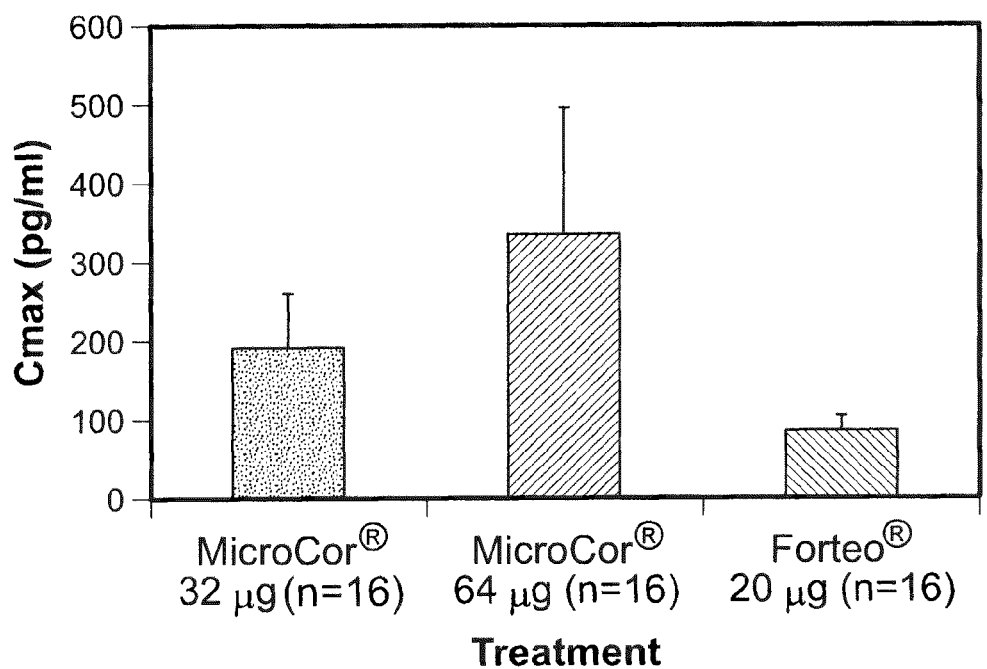
FIG. 5 is a graph illustrating mean Cmax (µg/mL) values for each of the three treatment regimes examined: an illustrative microprotrusion array-based hPTH transdermal delivery system (MicroCor® 32 µg dose and MicroCor® 64 µg dose) in comparison to subcutaneous administration (Forteo®, 20 µg dose) as described in detail in Example 11.
Figure 6:
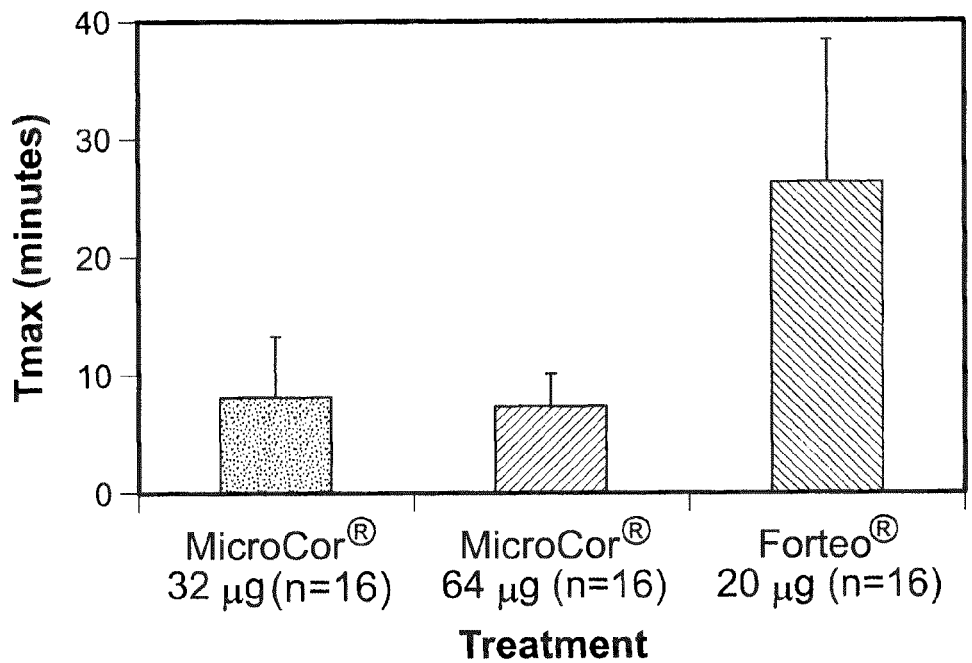
FIG. 6 is a graph illustrating mean Tmax (minutes) values for each of the three treatment regimes examined: an illustrative microprotrusion array-based hPTH transdermal delivery system (MicroCor® 32 µg dose and MicroCor® 64 µg dose) in comparison to subcutaneous administration (Forteo®, 20 µg dose) as described in detail in Example 11.

Dose-normalized area under the curve values in pg*min/mL*µg were calculated from the plasma concentration data, and are presented in FIG. 4. The AUC values for the exemplary microprotrusion array-based hPTH transdermal delivery system was approximately 48% lower than the AUC value for hPTH administered subcutaneously via injection. The lower AUC of the drug when administered via microneedles transdermally is indicative of the fast elimination half life, and supportive of this method of delivery being able to achieve the desirable pulastile delivery profile, wherein a pulse of drug is provided to the system with a rapid onset to maximum blood concentration and a fast elimination half-life of drug.

TABLE 1

Pharmacokinetic Results

| Parameter | MicroCor® 32 µg | MicroCor® 64 µg | Forteo® |
|---|---|---|---|
| AUC/Dose (pg * min/ mL * µg) | 220 (n = 15) | 229 (n = 16) | 429 (n = 16) |
| $C_{max}$(pg/mL) | 180 (n = 16) | 336 (n = 16) | 85 (n = 16) |
| $T_{max}$ (minutes) | 8.1 (n = 16) | 7.4 (n = 16) | 26.2 (n = 16) |
| Elimination Half-Life, $T_{1/2}$ (minutes) | 37.1 (n = 16) | 52 (n = 16) | 52 (n = 16) |

As can be seem from the data summarized in Table 1, relative to subcutaneously injected PTH, delivery transdermally via an array of microprojections exhibits rapid pharmacokinetic properties such as a shorter $T_{max}$, a higher $C_{max}$, and a shorter elimination half life, $T_{1/2}$. Absorption of hPTH (1-34) occurred more rapidly with the microprojection transdermal delivery relative to the subcutaneous delivery (Forteo®), as illustrated by the higher dose-normalized $C_{max}$ value and the smaller $T_{max}$ values for both microprojection transdermal delivery (MicroCor®) treatments.

Figure 8:
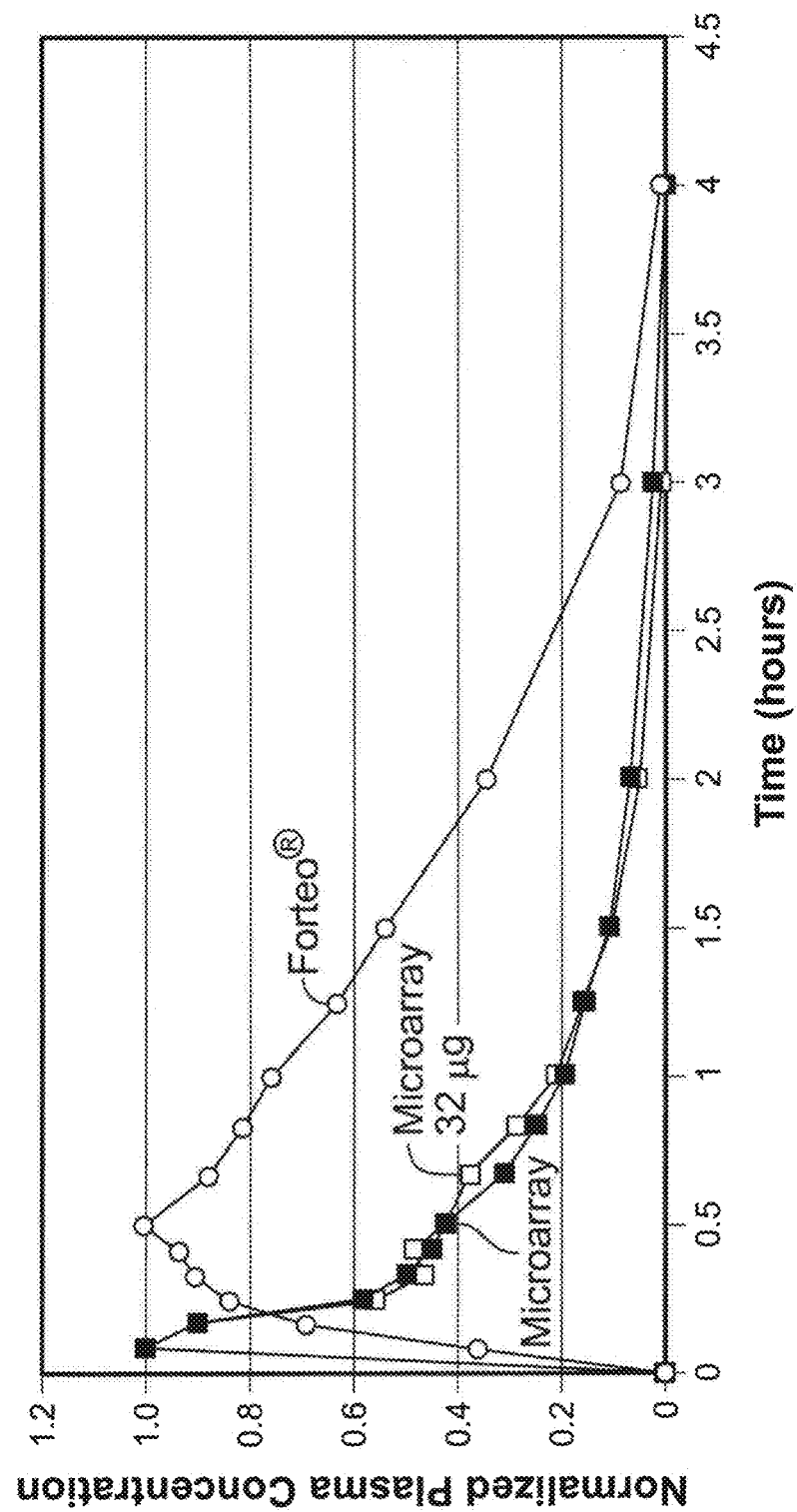
FIG. 8 is a graph illustrating normalized plasma concentration values versus time (hours) for each of the three treatment regimes examined: an illustrative microprotrusion array-based hPTH transdermal delivery system (MicroCor® 32 µg dose—open squares and MicroCor® 64 µg dose—closed squares) in comparison to subcutaneous administration (Forteo®, 20 µg dose, closed circles) as described in detail in Example 11.

FIG. 8 presents the pharmacokinetic data from the study of Example 11 in a different way, to illustrate the pulsatile delivery profile achieved with the microneedle array delivery system described herein. In FIG. 8, the plasma concentration value at each time point was normalized by the maximum concentration value achieved by each of the three treatment regimens: 32 microgram and 84 microgram doses of PTH delivered by the microprotrusion array and the 20 microgram dose delivered via subcutaneous injection. The Cmax normalized plasma concentration data is plotted against time, in hours. The time to achieve Cmax of well under 30 minutes when PTH is delivered transdermally from the microneedle array compared to the time to reach Cmax of greater than 30 minutes when administered subcutaneously is evident. The faster elimination of the drug after reaching Cmax when delivered transdermally from the microneedle array is also readily seen when the data is presented as shown in FIG. 8, by comparing the slopes of the lines during the elimination phase—i.e., at a time after Cmax.

In summary, relative to subcutaneous administration, the exemplary microprojection array-based PTH products described herein exhibit rapid pharmacokinetic properties. Such properties (relative to subcutaneous injection) include a shorter Tmax, a higher Cmax, and a shorter elimination half life, $T_{1/2}$. Ideally, administration using a microprojection array-based PTH product is effective to achieve a Tmax value that is at least about 2 times less, or at least about 3 times less, or at least about 4, or 5, or 6, or 7 times or more less than that achieved by SC administration of the same PTH moiety, preferably based upon normalized Cmax values. Absorption of hPTH (1-34) occurs more rapidly when delivered with the microprojection array-based delivery system when compared to delivery via subcutaneous injection (i.e., hPTH product Forteo®), as illustrated by the higher dose-normalized $C_{max}$ values and the faster $T_{max}$ values for both the high and low dose microprojection array-based treatments. The elimination half-life based upon microprojection array-based PTH treatment was also less than with subcutaneously administered PTH (Forteo®). Moreover, microprojection array-based treatment is more effective in achieving the desired pulsatile delivery profile of PTH (i.e., rapid on set and rapid offset after reaching Cmax), as can be seen in FIGS. 3 and 8.

The transdermal microprojection array delivery systems were analyzed after use, to assess residual PTH content in the microprojection array. Analysis for residual PTH in the arrays following application to a subject for delivery of the drug, revealed that, on average, about 85% of drug was delivered from the microprojection array device (i.e., 85% drug delivery efficiency, data not shown). Accordingly, in one embodiment, the method includes providing for use in the method a microprojection array capable of delivery at least about 55%, or at least about 60%, or at least about 65%, or at least about 70%, or at least about 75%, or at least about 80%, or at least about 85% of the total PTH dose in the array when applied to the skin of the patient for the desired amount of time. In the studies conducted above, the microarray was in contact with the skin for 5 minutes, however it will be appreciated that the microprojection array-delivery system can be applied to a skin site for times other than the 5 minutes utilized in the present study, in one embodiment, the system is maintained on the skin for no more than 15 minutes, or for no more than 10 minutes, or even for no more than 5 minutes. That is to say, the microprojection array is maintained on the skin for no more than about 15 minutes, or 14 minutes, or 13 minutes, or 12 minutes, or 11 minutes, or 10 minutes, or 9 minutes, or 8 minutes, or 7 minutes, or 6 minutes or even 5 minutes. Although any of a number of skin sites may be used for application of PTH such as the thigh, arm, etc., one preferred skin site is the abdomen.

A skilled artisan will also appreciate that delivery efficiency based on residual analysis of the microprojection array post-use is but one measure to characterize the device. The microprojection array can also be characterized by the percentage of total dose delivered by the microprojection array, determined for example based on pharmacokinetic parameters and the total amount of drug loaded into the microprojection array. This value may differ from a residual analysis since some of the drug delivered may be degraded by enzymes in the skin or not reach systemic circulation for other reasons. In one embodiment, the method for administering PTH to a human subject comprises contacting the skin of the subject with a microprotrusion array containing a dose of PTH and causing all or a portion, preferably a majority, of the microprotrusions to penetrate the stratum corneum. The microprotrusions in the array are left in contact with the skin for a period of time. Application of the device to the skin in accord with the method delivers at least about 40%, 45%, 50%, 55% or 60% of the total PTH dose in the microprotrusion array into systemic circulation of the subject. In another approach, the delivery efficiency of the microprojection array is determined based on comparing the pharmacokinetic parameters, and in particular AUC, to pharmacokinetic parameters achieved from a subcutaneously injected dose of PTH.

Methods of Use

The methods, kits, microprojection arrays and related devices described herein may be used for treating any condition receptive to treatment with PTH. For instance, the PTH-containing microprojection arrays may be used to deliver PTH for treatment of osteoporosis, osteopenia, periodontal disease, and in particular, periodontal disease associated with alveolar bone loss. The PTH-containing microprojection arrays are also contemplated for use in healing bone fractures, improving bone fracture healing rates and for reducing risk of fracture in at risk persons.

More particularly, the methods, kits, microprojection arrays and related devices described herein may be used for (i) treating postmenopausal women with osteoporosis at high risk for fracture, (ii) increasing bone mass in men with primary or hypogonadal osteoporosis at high risk for fracture, (iii) treatment of osteoporosis in men and women with osteoporosis associated with sustained glucocorticoid therapy at high risk for fracture, and (iv) treatment of osteoporotic patients who have failed or are intolerant of other available osteoporosis therapies.

It is to be understood that while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not necessarily to the text of this application, in particular the claims of this application, in which instance, the definitions provided herein are meant to supercede.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

General Process for Array Casting

A clean mold is placed in a mold folder. The mold is then placed in a Petri dish and a small amount of formulation, for example, 200 µL, is placed on the mold. An illustrative formulation such as those described herein is applied. The formulation is spread manually over the mold using a transfer pipette with a trimmed tip. The formulation is then vortexed, for example, for five seconds, using a commercial vibrating instrument. The mold containing formulation is placed in a pressure vessel under 1 atm for about 1 minute. Pressure is released, and the mold placed in an incubator at 32° C., for about 1 hr. The array is then demolded, for example, using double-sided adhesive tape, and optionally attached to a backing.

EXAMPLE 2

General Process for Casting Two-Layer Arrays

Following the drying step of Example 1, an additional layer is cast on the mold using similar procedures. An exemplary composition, e.g., containing 75 µL of 20 wt % Eudragit® EPO in a 3:1 mixture of ethanol and isopropyl alcohol is cast onto the mold. The additional layer may be spread out, for example, using a glass slide. The mold containing the additional layer is placed in a pressure vessel and pressurized at 1 atm for 2 minutes. The pressure is released and the mold is allowed to dry in the pressure vessel for an additional five minutes, without disturbing. The mold is again dried in the incubator for 1 hr at 32° C., and then demolded.

EXAMPLE 3

Casting Two-Layer Arrays

A microprojection array with two layers is typically prepared by the following steps.

Step 1. Casting a Solution Comprising an Active Agent, Polymer, and possibly other components in a mold.

The clean mold is placed in a mold holder. A small amount of formulation, for example, 75 as a droplet on the mold, is dispensed by placing a cover slip on top of the droplet to help spread the liquid onto the entire surface of the mold. An exemplary wet formulation contains, for example, 15% human parathyroid hormone 1-34 fragment (hPTH1-34), 65% dextran 70 and 20% sorbitol, in a histidine buffer solvent with a total solids content of 30% as applied to the mold. The loaded mold (i.e., containing drug formulation) is placed in a pressure vessel under about 50 psi for about 30 seconds. Pressure is then removed. The excess formulation is wiped with a silicone or metal wiper with the interference between wiper edge and surface of mold about 1-10 mils. The mold is placed in an incubator at a temperature of 32° C., for about half an hour. After incubating, the dry formulation contains 5% human parathyroid hormone 1-34 fragment (hPTH1-34), 21% dextran 70 and 7% sorbitol, with histidine and histidine hydrochloride also present.

Step 2. Casting an Additional Layer on Top of the First Layer in the Mold.

The mold with drug-containing layer cast is removed from the drying oven, and any residue of dry formulation left on the base of the mold is removed by tape strip using a 3M 1516 single-sided adhesive. Approximately 150 µL of "backing" or upper layer/base solution containing poly (lactic acid-co-glycolic acid) (PLGA) with an L/G ratio of 75/25 in acetonitrile is placed on the mold (atop the first drug-containing formulation). A thin film is cast using a wiper with the clearance between edge of the wipe and the surface of the mold about 10-20 mil. The mold is then placed into a pressure vessel under 10-30 psi with controlled venting for about 5 min. The mold is further dried at room temperature for about 30 min. The array may then be demolded, for example using double-sided adhesive tape, and optionally attached to a polyethylene terephthalate film as backing.

EXAMPLE 4

Solvent-Cast Microprojection Arrays Containing hPTH(1-34)

Microprojection arrays were prepared according to the general procedures described above. The following table provides the relative amounts of water-soluble matrix components and active agent, along with the percent solids content of the resulting exemplary casting solutions.

TABLE 4-1

| Ex. # | Polymer | | Sugar | | hPTH (1-34) | Solids in casting solution |
|---|---|---|---|---|---|---|
| | Type | Wt % | Type | Wt % | Wt % | Wt % |
| B1 | PVA | 52.6 | Sucrose | 26.3 | 21.1 | 22.8 |
| B2 | PVA | 46.2 | Sucrose | 23.1 | 30.7 | 26 |
| B3 | Dextran 70 | 67.5 | Sorbitol | 14 | 18.5 | 33 |
| B4 | Dextran 70 | 64.9 | Sorbitol | 19.5 | 15.6 | 30.8 |
| B5 | Dextran 40 | 67.5 | Sorbitol | 14 | 18.5 | 33 |
| B6 | Dextran 40 | 64.9 | Sorbitol | 19.5 | 15.6 | 30.8 |
| B7 | Tetrastarch | 67.5 | Sorbitol | 14 | 18.5 | 33 |
| B8 | Tetrastarch | 64.9 | Sorbitol | 19.5 | 15.6 | 30.8 |
| B9* | Dextran 70 | 64.8 | Sorbitol | 19.3 | 15.5 | 31.2 |

*ca. 0.4 wt % of methionine was added to the formulation as an antioxidant agent.

Based on the above, it can be seen that a wide variety of formulations can be prepared for use in forming a microprojection arrays for delivery of hPTH through the skin.

EXAMPLE 5

Polymeric Solution for Casting "Backing" or Upper Layers of Microneedle Arrays

For arrays comprising an upper microprotrusion portion or layer proximal to the base of the array and placed atop the water soluble polymer/hPTH tip layer), different polymer formulations were used. The backing layer (which in this embodiment comprises the upper portion of the microprotrusion proximal to the base and the base itself) comprises one or more water-insoluble polymers. The polymer solutions were typically prepared by dissolving the polymers in a solvent or solvent mixture at room temperature with a polymer concentration ranging from about 15-30% by weight.

The details of the illustrative polymer solutions used for casting the backing layer of the microneedle arrays are summarized in the table below.

TABLE 5-1

| Ex. # | Polymer | | Solvent | |
|---|---|---|---|---|
| | Type | Wt % | Type | Wt % |
| C1 | Eudragit EPO 100 | 20 | Ethanol/IPA | 80 |
| C2 | Eudragit EPO 100 | 30 | Ethanol/IPA 3/1 | 70 |
| C3 | Eudragit EPG 100/PVP (1:1) | 20 | Ethanol/IPA 3/1 | 80 |
| C4 | PLGA (75/25) | 10 | Ethyl acetate | 90 |
| C5 | PLGA (75/25) | 15 | Ethyl acetate | 85 |
| C6 | PLGA (75/25) | 15 | Acetonitrile | 85 |
| C7 | PLGA (75/25) | 20 | Acetonitrile | 80 |
| C8 | PLGA (75/25) | 30 | Acetonitrile | 70 |
| C9 | PLGA (65/35) | 20 | Acetonitrile | 80 |
| C10 | PLA | 20 | Acetonitrile | 80 |
| | Polycaprolactone | 20 | Acetonitrile | 80 |

In the table above, the following abbreviations are used: Polyvinylpyrrolidone (PVP); poly(lactic acid-co-glycolic acid) (PLGA) (L/G ratio 75/25, 65/35): poly(lactic acid) (PLA); and isopropyl alcohol (IPA).

EXAMPLE 6

Casting Microneedle Arrays with Three Layers

A microneedle array with three layers is prepared as follows.

1) Casting a non-drug containing tip layer (end portion distal to base) in the mold.

The clean mold is placed in a mold holder. A small amount (200 µL) of formulation solution absent drug is dispensed as a droplet on the mold. One such exemplary formulation contains, for example, 23% dextran 70, 10% sorbitol in histidine buffer solvent, such that the formulation has, e.g., a 30% solids content as applied. The mold comprising formulation is placed in a pressure vessel under ca. 50 psi for about 30 seconds. Pressure is then released. Any excess formulation is wiped with a silicone or metal wiper with the interference between wiper edge and surface of the mold at about 1-10 mils. The mold is placed in an incubator at a temperature of 32° C., for about half an hour.

2) Casting Drug Containing Layer in the Mold.

After step 1) above, a small amount of formulation, for example, 75 µL, is dispensed as a droplet on the mold. A cover slip is placed on top of the droplet to aid in spreading the liquid onto the entire surface of the mold. One such illustrative formulation may contain, for example, on a dry weigh basis 5% wt human parathyroid hormone 1-34 fragment (hPTH(1-34)), 21% wt dextran 70, 7% wt sorbitol. The wet casting formulation utilizes histidine buffer as the solvent, such that the formulation has, for example, a 30% solids content as applied. The mold containing is then placed in a pressure vessel under ca. 50 psi for about 30 seconds. Pressure is then released. The excess formulation is wiped with a silicone or metal wiper with the interference between wiper edge and surface of mold about 1-10 mils. The mold is placed in an incubator at a temperature of 32° C., for about half an hour.

3) Casting the Backing Layer on Top of the Drug-Containing Layer.

After step 2) above, about 150 µL of backing solution (upper layer portion) comprising poly(lactic acid-co-glycolic acid) (PLGA) with a L/G ratio of 75/25 in acetonitrile is placed on the mold (on top of the drug-containing layer). A thin film is cast using a wiper with the clearance between edge of the wipe and surface of the mold about 10-20 mil. The mold is then placed into a pressure vessel under 10-30 psi with controlled venting for about 5 min. The mold is further dried at room temperature for about 30 min. The array is then demolded, for example using double-sided adhesive tape, and optionally attached to a polyethylene terephthalate film as backing.

EXAMPLE 7

Casting Arrays for Sustained Release of Drug Substance from the Array

A microneedle array for sustained release of drug substance from the array is prepared in the following steps.

1) Casting a Drug-Containing Layer for Sustained Release of Drug Substance.

A clean mold is placed in a mold holder. A small amount (e.g., 75 µL) of aqueous solution containing, e.g., hPTH(1-34), components for a polymeric matrix such as polyethylene glycol-co-poly(lactic acid-co-glycolic acid) (PEG-PLGA) copolymer, and excipients such as sucrose or sorbitol, is dispensed into the mold. The polymeric matrix is generally amphiphilic in nature, where the hydrophobic segment(s) of the polymer are effective to control the release of drug substance. Exemplary formulations of this type are described in the table below. The liquid formulation is spread manually on the surface of the mold with a glass cover slip. The formulation-loaded mold is placed in a pressure vessel under ca. 50 psi for about 30 seconds. Pressure is then released. Excess formulation is wiped with a silicone or metal wiper with the interference between wiper edge and surface of the mold about 1-10 mils. The mold is placed in an incubator at room temperature for about half an hour.

The following table provides the details of representative aqueous solutions used to form this type of microneedle array comprising drug substance hPTH, a polymeric matrix, and excipients.

TABLE 7-1

| Ex. # | Polymer Type | Wt % | Excipients Type | Wt % | hPTH (1-34) Wt % | Solids in casting solution Wt % |
|---|---|---|---|---|---|---|
| D1 | PEG-PLGA (50/50(65/35)) | 50 | Sucrose | 35 | 15 | 10 |
| D2 | PEG-PLGA (50/50(65/35)) | 45 | Sucrose | 40 | 15 | 10 |
| D3 | PEG-PLGA (50/50(65/35)) | 45 | Sucrose | 40 | 15 | 20 |
| D4 | PEG-PLGA (50/30(65/35)) | 55 | Sucrose | 35 | 10 | 10 |
| D5 | PEG-PLGA (50/30(65/35)) | 55 | Sucrose | 35 | 10 | 10 |
| D6 | PEG-PLGA (50/30(65/35)) | 55 | Sorbitol | 35 | 10 | 10 |
| D7 | PEG-PLGA (50/50(65/35)) | 45 | Sorbitol | 40 | 15 | 10 |
| D8 | Pluronic F68 | 50 | Sucrose | 35 | 15 | 25 |
| D9 | Pluronic F127 | 50 | Sucrose | 35 | 15 | 15 |
| D10 | Pluronic F68 | 50 | Sorbitol | 35 | 15 | 25 |
| D11 | Pluronic F127 | 50 | Sorbitol | 35 | 15 | 15 |

In the table above, PEG-PLGA denotes a blend of polyethylene glycol and poly(lactic acid-co-glycolic acid).

2) Casting Dissolvable Layer on Top of the Drug-Containing Layer in the Mold.

After step 1) above, a small amount of formulation, for example, 25 μL, is placed as a droplet on the mold, and a cover slip is placed of top of the droplet to spread the liquid onto the entire surface of the mold. For example, an illustrative wet formulation contains 70% Dextran 70, and 30% sorbitol, in histidine buffer solvent, such that the formulation contains, for example, 30% solids content as applied. The drug-polymer matrix loaded mold is placed in a pressure vessel under ca. 50 psi for about 30 seconds. Pressure is then released. Excess formulation is wiped with a silicone or metal wiper with the interference between wiper edge and the surface of the mold about 1-8 mils. The mold is placed in an incubator at a temperature of 32° C., for about half an hour.

3) Casting Backing Layer on Top of the Dissolvable Layer in the Mold.

Following step 2) above, approximately 150 μL of backing solution (upper portion lay r) containing poly(lactic acid-co-glycolic acid) (PLGA) with a L/G ratio of 75/25 in acetonitrile is placed on the mold (on top of the dissolvable layer) and a thin film is cast using a wiper with the clearance between edge of the wipe and surface of mold about 10-20 mil. The mold is then placed into a pressure vessel under 10-30 psi with controlled venting for about 5 min. The mold is further dried at room temperature for about 30 min. The array is demolded, for example using double-sided adhesive tape, and optionally attached to a polyethylene terephthalate film as backing.

EXAMPLE 8 hPTH(1-34) Stability in Dry Films Made with Microneedle Casting Formulations

Dry films of microneedle casting formulations were prepared using process conditions similar to those for casting microneedle arrays to evaluate the stability of hPTH (1-34 fragment) in the dried form. About 200 μL of liquid formulation was placed in an Eppendorf tube. The formulation was spread into a thin film in the inside wall of the tube, then dried at 32° C. for 30 min, and then further dried under vacuum at room temperature overnight. The dry films inside the Eppendorf tube were packaged in a polyfoil bag and stored at different temperatures for different durations. The purity of the hPTH(1-34) was analyzed by both reverse phase HPLC (rp-HPLC) and size exclusion HPLC (sec-HPLC). The details of the formulations are indicated in Table 8-1 below.

The following table provides details of the formulations used to form dry films containing hPTH as the active agent.

TABLE 8-1

| Ex. # | Polymer Type | Wt % | Sugar Type | Wt % | hPTH (1-34) Wt % | Solids in casting solution Wt % |
|---|---|---|---|---|---|---|
| F1 | PVA | 52.6 | Sucrose | 26.3 | 21.1 | 22.8 |
| F2 | Dextran 70 | 64.9 | Sorbitol | 19.5 | 15.6 | 30.8 |
| F3 | Tetrastarch | 64.9 | Sorbitol | 19.5 | 15.6 | 30.8 |
| F4* | Dextran 70 | 64.1 | Sorbitol | 19.4 | 15.4 | 31.2 |

*ca. 0.4 wt % of methionine was added to the formulation as an antioxidant agent.

Table 8-2 below illustrates the chemical purity as determined by rp-HPLC of the hPTH(1-34) in different formulations as a function of storage time at three different temperatures. Table 8-3 below illustrates the monomer content as determined by sec-HPLC of the hPTH(1-34) in different formulations as a function of storage time at three different temperatures. It appears that hPTH(1-34) is stable during storage for up to one month at even elevated temperature in all the formulations examined. (Formulation F3 was not sampled at the 1 week time point at room temperature or 40° C.)

TABLE 8-2

| | F1 | F2 | F3 | F4 |
|---|---|---|---|---|
| 5° C. | | | | |
| t = 0 | 100.0 | 100.0 | 100.0 | 100.0 |
| t = 1 week | 99.77 | 99.87 | 99.78 | 100.00 |
| t = 2 week | 99.76 | 99.71 | 99.65 | 99.74 |
| t = 1 month | 99.78 | 99.69 | 99.66 | 99.73 |
| t = 13 months | 98.87 | 100.0 | 100.0 | 100.0 |
| 25° C. | | | | |
| t = 0 | 100.0 | 100.0 | 100.0 | 100.0 |
| t = 1 week | 99.75 | 100.0 | | 100.0 |
| t = 2 week | 99.72 | 99.63 | 99.49 | 99.70 |
| t = 1 month | 99.72 | 99.59 | 99.52 | 99.67 |
| t = 3 months | 99.76 | 99.72 | 99.09 | 99.88 |
| t = 13 months | 100.0 | 98.62 | 99.11 | 98.58 |
| 40° C. | | | | |
| t = 0 | 100.0 | 100.0 | 100.00 | 100.00 |
| t = 1 week | 99.72 | 99.79 | | 99.88 |
| t = 1 month | 99.56 | 99.14 | 98.64 | 99.39 |

TABLE 8-3

|  | F1 | F2 | F3 | F4 |
|---|---|---|---|---|
| 5° C. | | | | |
| t = 0 | 100.00 | 100.00 | 100.00 | 100.00 |
| t = 1 week | 99.77 | 99.87 | 99.78 | 100.00 |
| t = 2 week | 99.76 | 99.71 | 99.65 | 99.74 |
| t = 1 month | 99.78 | 99.69 | 99.66 | 99.73 |
| 25° C. (room temp.) | | | | |
| t = 0 | 100.00 | 100.00 | 100.00 | 100.00 |
| t = 1 week | 99.75 | 100.00 | | 100.00 |
| t = 2 week | 99.72 | 99.63 | 99.49 | 99.70 |
| t = 1 month | 99.72 | 99.59 | 99.52 | 99.87 |
| t = 3 months | 99.70 | 99.67 | 99.52 | 99.77 |
| 40° C. | | | | |
| t = 0 | 100.00 | 100.00 | 100.00 | 100.00 |
| t = 1 week | 99.72 | 99.79 | | 99.88 |
| t = 1 month | 99.56 | 99.14 | 98.84 | 99.39 |

EXAMPLE 9

Preparation of a 2-Layer Microprojection Array Containing Human Parathyroid Hormone (hPTH(1-34))

A microprojection array containing a therapeutically effective amount of hPTH(1-34) (32 μg) was prepared for use in a Phase I clinical study as follows.

First, in describing generally the features of the microprojection array, the microprotrusions of the array can be characterized generally as comprising a DIT (drug-in-tip) layer and a "backing" layer. The DIT layer includes hPTH(1-34) in a water-soluble matrix. The sequence of hPTH(1-34) used was:

(SEQ ID NO: 1)
H-Ser-Val-Ser-Glu-Ile-Gln-Leu-Met-His-Asn-Leu-
Gly-Lys-His-Leu-Asn-Ser-Met-Glu-Arg-Val-Glu-Trp-
Leu-Arg-Lys-Lys-Leu-Gln-Asp-Val-His-Asn-Phe-OH

The tip of the microprojections is also referred to herein as the layer at the bottom-most portion of the tips or microprotrusions (i.e., proximal to the skin when placed upon the skin), also referred to herein as the "end portion" that is distal to the base of the array). The "backing" layer as referred to in certain of these examples, encompasses both the upper portion of the microprotrusions proximal to the base of the array as well as the base itself, where the base is the portion of the array that supports the tips. The backing layer comprises a biocompatible, non-water soluble matrix. In the instant array device, the material in the upper portion of the microprotrusions is the same as the base material itself, so that the non-water soluble matrix formulation is applied as a single layer to fill the mold atop the DIT layer.

The DIT layer of the microstructure array dissolves into the skin and contains the components provided in Table 9-1. Acetate was the counter-ion in the hPTH(1-34) drug substance.

TABLE 9-1

Composition of Drug-in-Tip Layer of hPTH(1-34) TDS

| Trade Name | Chemical Name of Ingredient | Quantity (μg/unit) | Range (μg/unit) | % w/w (of the microstructure array) |
|---|---|---|---|---|
| hPTH (1-34) | human Parathyroid hormone (1-34) | 32.0 | 25.6-38.4 | 12.8 |
| Dextran 70 | Dextran, 70,000 Dalton molecular weight | 160.0 | 128.0-192.0 | 58.6 |
| Sorbitol, N.F. | Sorbitol | 54.9 | 64.0-96.0 | 21.9 |
| Histidine | L-histidine | 0.14 | 0.11-0.17 | 0.1 |
| Histidine HCl | L-histidine hydrochloride | 0.73 | 0.58-0.88 | 0.3 |
| NA | Acetate | 2.5 | 2.0-3.0 | 1.0 |
| Total | | 250.27 | | 100.0 |

The backing portion or layer of the array was composed of poly(DL-lactide-co-glycolide), 75:25, ester terminated (Tradename: LACTEL®).

The ingredients forming the tip portion of the formulation (i.e., the DIT formulation) were dissolved in water, cast, and dried in a silicone mold containing microstructure cavities to form the drug-in-tips (DIT) structures. The water insoluble, biocompatible polymer, poly(DL-lactide-co-glycolide), 75:25, was dissolved in acetonitrile to provide the backing formulation which was then coated on top of the DIT layer in the silicone mold, and then dried. The solvent was removed from the backing (upper portion proximal to the base, and base) during processing and was limited to a level below the amounts recommended in ICH residual solvent guidelines.

EXAMPLE 10

Preparation of a Delivery Device Containing a Microprojection Array Containing Human Parathyroid Hormone (hPTH(1-34))

A delivery system, also referred to as an applicator-array assembly, comprising a microprojection array prepared in accord with Example 9 and an applicator as described with reference to FIGS. 1-2, was assembled as follows. A microprojection holding member with a microprojection array (Example 9) was prepared and packaged, and separately an applicator assembly (i.e., an applicator as in FIGS. 1-2 absent the microprojection-holding member) was packaged. The two separate packages were provided in a single boxed unit to each clinical site, for assembly of the applicator-array assembly prior to use on a patient (see Example 11 below for clinical data).

The microprojection array contained was 11 millimeters in diameter with approximately 2700 microprojections arranged in a hexagonal pattern. The microprojection array was mounted on the microprojection-holding member (element 184 of FIG. 2) using an adhesive laminate. The microprojection-holding member/microprojection array was packaged inside a protective container and pouched in a dry nitrogen environment.

The applicator assembly comprised of an outer housing (element 182 of FIG. 2) with a skin contact adhesive and a release liner (elements 192, 194, respectively, of FIG. 2), an energy storage member (in this case, a metal wave spring), and elements to hold these items together. This applicatory assembly was packaged inside a protective container and pouched.

Prior to use of the system, the microprojection-holding member/microprojection array was inserted into the applicator assembly, and the system was activated by compressing the spring and then twisting the microprojection-holding member to lock and hold the compressed spring in place in the applicator. To initiate delivery of the hPTH dose, the user twists the microprojection-holding member to unlock or unseat it from the outer cover, thus causing the spring to release its stored energy causing accelerated movement of the microprojection-holding member and attached microprojection array into contact with the skin. Upon contact with the skin, the microstructures penetrate past the stratum corneum, and the hPTH dissolves into the skin rapidly. Following actuation of the spring and delivery of hPTH, the system is removed and discarded.

EXAMPLE 11

In-Vivo Study: Administration of Human Parathyroid Hormone hPTH(1-34) Via a Microprojection Array Device in Healthy an Subjects An open label, single dose, sequence randomized, 3-way cross-over study was carried out in sixteen healthy female volunteers to determine the pharmacokinetics (along with additional secondary endpoints) of 32 µg hPTH(1-34) and 64 µg hPTH(1-34) (32 µg hPTH(1-34)×2) delivered using the TDS ("MicroCor®") described in Examples 9 and 10 relative to subcutaneously administered (SC) FORTEO® (teriparatide), 20 µg. The system described in Examples 9 and 10 is referred to in this example generally as "MicroCor® hPTH(1-34)" or for simplicity herein, "MicroCor®".

Subjects received a single dose of 32 µg hPTH(1-34) or 64 µg hPTH(1-34) (32 µg×2) by applying the MicroCor® device to an abdominal site for 5 minutes. Treatment with the commercial hPTH product known as Forteo® was accomplished by administration as a subcutaneous injection into the abdominal wall. Treatments were separated by a 48-hour washout period. The plasma sampling schedule was as follows: pre-treatment, 5, 10, 15, 20, 25, 30, 40, 50, 60, 75, 90, 120, 180, 240, 300, 360 minutes, and 24 hours post-treatment. Vital signs were monitored pre-treatment, and at 15 and 30 minutes, and 1, 2, 3, 4, 5, 6, 8, 10, 12, and 24 hours post-treatment. Adverse advents were monitored throughout the study. Additional assessments included (i) measurement of anti-PTH antibodies prior to first treatment and 2 weeks following last treatment, (ii) measurement of serum calcium, phosphorous, albumin, and protein at pre-treatment, and 1, 2, 3, 4, 5, 6, and 24 hours post-treatment, as well as (iii) adhesion of the MicroCor® system.

Administration of hPTH transdermally via the microarray (MicroCor® treatments) demonstrated good skin tolerability. Skin effects were transient and well-tolerated, with mild to moderate erythema observed. In terms of general safety, all treatment regimes were well-tolerated. No significant adverse events nor unexpected adverse events occurred. In fact, there was no difference in the overall treatment-related adverse events between the MicroCor® and the Forteo®-based treatments. No significant changes were observed in serum calcium, and no anti-PTH antibodies were detected, again further demonstrating the overall safety of MicroCor®-based treatment in human subjects. Data is presented in FIGS. 3-8 and Table 1, above.

It is claimed:

1. A method of transdermally administering a dose of PTH to a mammalian subject, comprising:
   applying to a skin site of a subject a microprotusion array comprising a plurality of microprotrusions extending from an approximately planar base, each microprotrusion comprising an end portion distal to the base and an upper portion proximal to the base, the end portion comprising a tip of the microprotrusion, at least the end portion comprising parathyroid hormone (PTH) in a water-soluble polymer matrix,
   inserting all or a portion of the plurality of microprotrusions into the skin, and
   maintaining the array on the skin site for 15 minutes or less, whereby at least a portion of the end portions including the tip of the plurality of microprotrusions detach from the microprotrusion array;
   whereby the method achieves an average time to maximum PTH plasma concentration ($T_{max}$) of about ten minutes or less.

2. The method of claim 1, wherein the PTH is human parathyroid hormone (1-34).

3. The method of claim 1, wherein the water-soluble polymer matrix comprises a sugar selected from the group consisting of dextran and sorbitol.

4. The method of claim 3, wherein the water-soluble matrix further comprises a buffer selected from the group consisting of histidine and histidine hydrochloride.

5. The method of claim 1, wherein the base is comprised of a water-insoluble polymer.

6. The method of claim 5, wherein the upper portion of each microprotrusion is comprised of the water-insoluble polymer.

7. The method of claim 5, wherein the water-insoluble polymer comprises a poly(lactic acid-co-glycolic acid).

8. The method of claim 6, wherein the water-insoluble polymer comprises a poly(lactic acid-co-glycolic acid).

9. The method of claim 1, wherein the end portion and the upper portion of each microprotrusion are comprised of the same water-soluble polymer.

10. The method of claim 5, wherein the end portion and the upper portion of each microprotrusion are comprised of the same water-soluble polymer.

11. The method of claim 1, wherein at least about 80% of a dose of PTH in the microprotrusion array is in the end portions of each microprotrusion in the plurality of microprotrusions.

12. The method of claim 1, wherein the steps of applying and inserting occur at an abdominal skin site.

13. The method of claim 1, whereby the method is effective to achieve an elimination half-life that is less than about 45 minutes.

14. The method of claim 1, whereby the method is effective to achieve an elimination half-life that is at least about 20% faster than the elimination half life achieved with the same, or lower dose, of PTH delivered via subcutaneous injection.

* * * * *

UNITED STATES PATENT AND TRADEMARK OFFICE
CERTIFICATE OF CORRECTION

PATENT NO. : 9,687,641 B2
APPLICATION NO. : 13/101071
DATED : June 27, 2017
INVENTOR(S) : Singh et al.

It is certified that error appears in the above-identified patent and that said Letters Patent is hereby corrected as shown below:

In the Claims

In Claim 1, Column 28, Line 48: change "microprotusion" to --microprotrusion--.

Signed and Sealed this
Twenty-first Day of November, 2017

Joseph Matal
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 1

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe
```